United States Patent
Toner et al.

(10) Patent No.: US 9,170,646 B2
(45) Date of Patent: Oct. 27, 2015

(54) OPHTHALMIC LENS SYSTEM CAPABLE OF INTERFACING WITH AN EXTERNAL DEVICE

(71) Applicant: Johnson & Johnson Vision Care, Inc., Jacksonville, FL (US)

(72) Inventors: Adam Toner, Jacksonville, FL (US); Randall Braxton Pugh, St. Johns, FL (US); Camille A. Higham, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 177 days.

(21) Appl. No.: 14/017,722

(22) Filed: Sep. 4, 2013

(65) Prior Publication Data

US 2015/0061990 A1  Mar. 5, 2015

(51) Int. Cl.
  *G09G 5/00* (2006.01)
  *G06F 3/01* (2006.01)
  *G06F 3/0346* (2013.01)
  *G06F 3/03* (2006.01)
  *G02C 7/04* (2006.01)
  *H04W 4/00* (2009.01)

(52) U.S. Cl.
  CPC .............. *G06F 3/013* (2013.01); *G02C 7/04* (2013.01); *G06F 3/016* (2013.01); *G06F 3/0317* (2013.01); *G06F 3/0346* (2013.01); *H04W 4/001* (2013.01); *H04W 4/008* (2013.01); *A61F 2250/0001* (2013.01); *G02B 2207/123* (2013.01)

(58) Field of Classification Search
  None
  See application file for complete search history.

(56) References Cited

U.S. PATENT DOCUMENTS

| 2009/0244477 A1 | 10/2009 | Pugh | |
|---|---|---|---|
| 2010/0103369 A1 | 4/2010 | Pugh | |
| 2010/0110372 A1* | 5/2010 | Pugh et al. | 351/177 |
| 2011/0084834 A1* | 4/2011 | Sabeta | 340/540 |
| 2012/0019995 A1 | 1/2012 | Tsai | |
| 2012/0245444 A1 | 9/2012 | Otis | |

FOREIGN PATENT DOCUMENTS

| CA | 2717328 A1 | 4/2012 |
|---|---|---|
| EP | 2620802 A1 | 7/2013 |
| WO | WO2008109867 A3 | 10/2008 |

OTHER PUBLICATIONS

European Search Report dated Jan. 28, 2015 for corresponding EPA No. 14183606.4.

* cited by examiner

*Primary Examiner* — Muhammad N Edun

(57) ABSTRACT

The present invention provides an energizable ophthalmic lens system capable of wirelessly interfacing with an external device. The energizable ophthalmic lens system may dynamically interact with a specified external device, wherein a user may operate one or more functionalities within the external device through the energizable ophthalmic lens system. The external device may be able to recognize eye gestures, which may comprise deliberate eye and lid movements. The external device may operate a functionality within the ophthalmic lens system, wherein the operation may be based on information received from the ophthalmic lens system. The ophthalmic lens system may comprise at least one energizable ophthalmic lens. Multiple ophthalmic lenses may be preferable where the functionality of either or both the ophthalmic lens system or the external device may occur based on relative position data or communication between lenses.

28 Claims, 10 Drawing Sheets

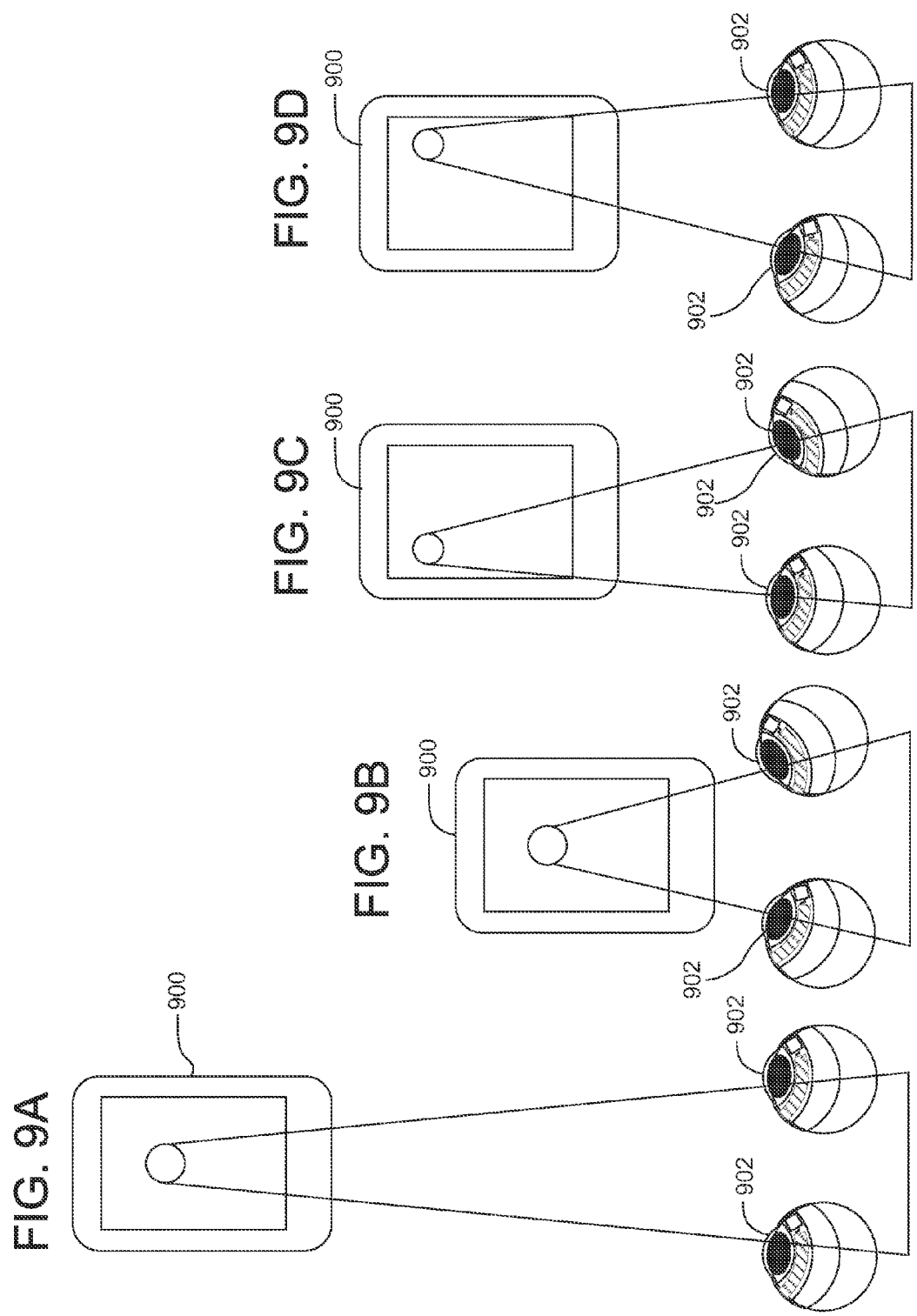

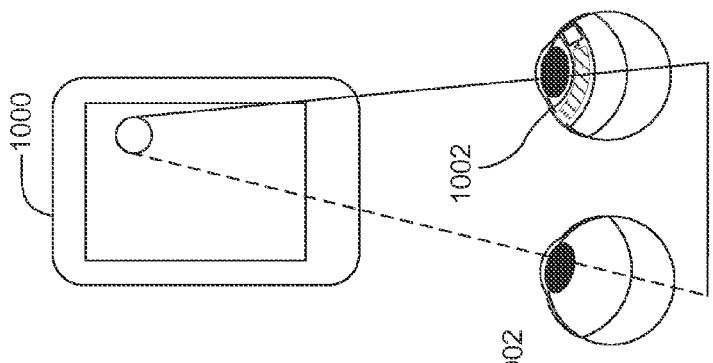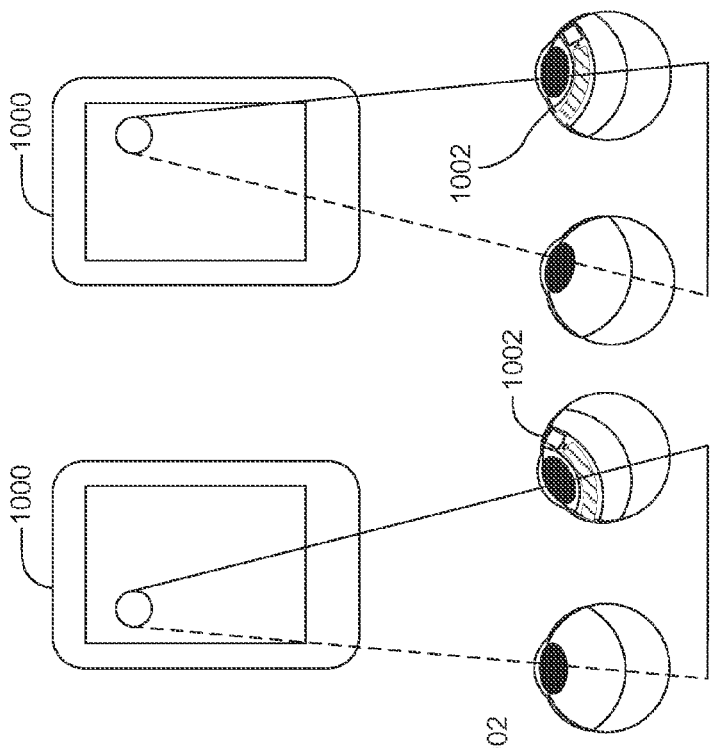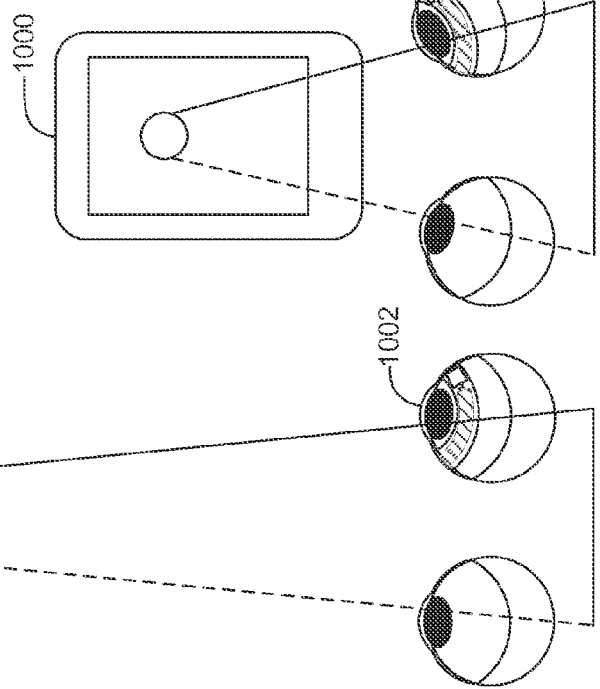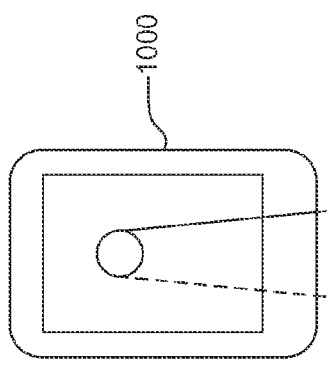

FIG. 11A
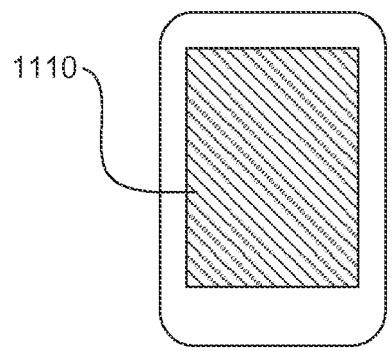
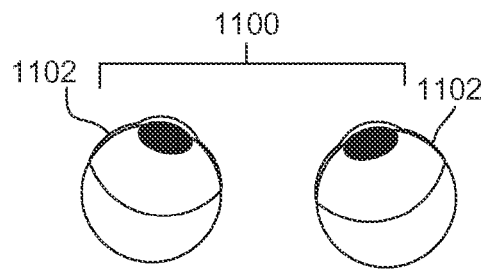
FIG. 11B
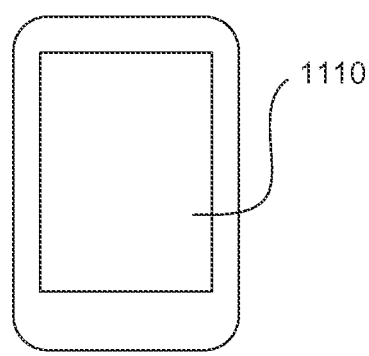
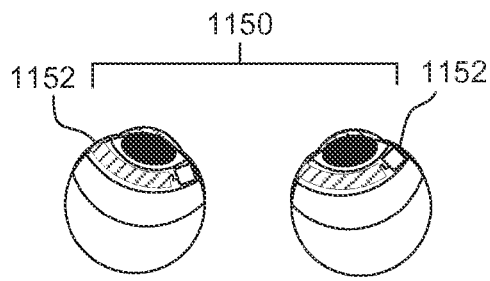
FIG. 12
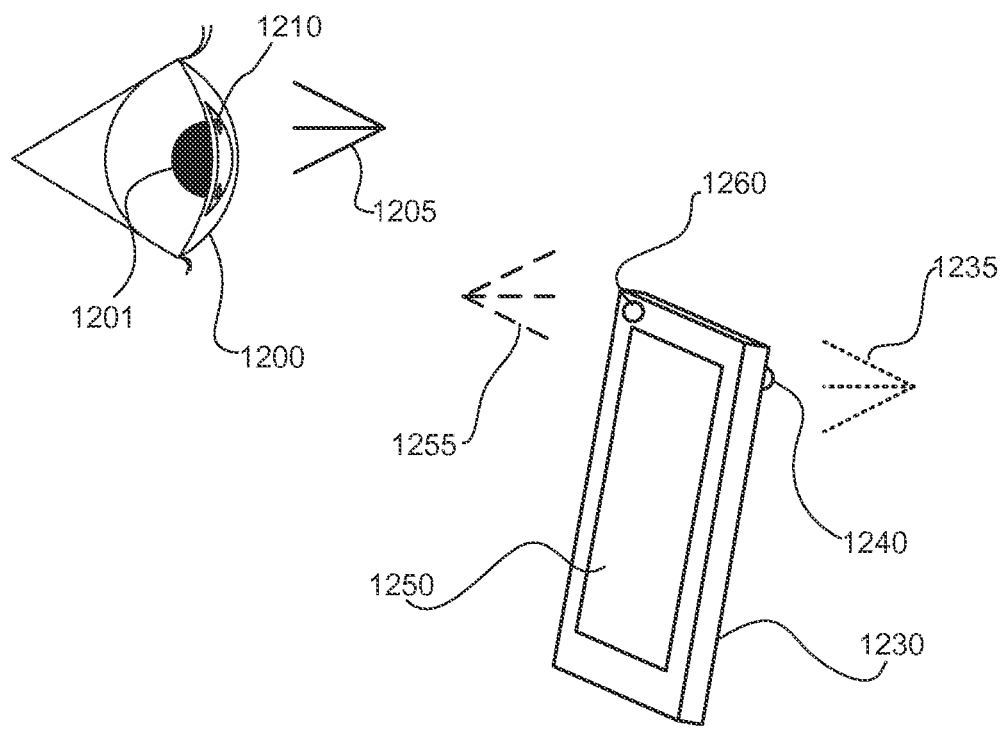

OPHTHALMIC LENS SYSTEM CAPABLE OF INTERFACING WITH AN EXTERNAL DEVICE

BACKGROUND OF THE INVENTION

1. Field of the Invention

The present invention relates to methods, apparatus, and devices associated with ophthalmic lenses that may interface with an external device, including, for example, smartphones, televisions, or laptop computers. More particularly, the present invention relates to an energizable ophthalmic lens system that may dynamically interact with the functions of an external device with a screen and an operating system.

2. Discussion of the Related Art

Traditionally, an ophthalmic device, such as a contact lens, an intraocular lens, or a punctal plug included a biocompatible device with a corrective, cosmetic, or therapeutic quality. A contact lens, for example, may provide one or more of vision correcting functionality, cosmetic enhancement, and/or therapeutic effects. Each function is provided by a physical characteristic of the lens. A design incorporating a refractive quality into a lens may provide a vision corrective function. Pigmentation incorporated into the lens may provide a cosmetic enhancement. An active agent incorporated into a lens may provide a therapeutic functionality. Such physical characteristics may be accomplished without the lens entering into an energized state.

Recently, active components have been included in a contact lens, and the inclusion may involve the incorporation of energizing elements within the ophthalmic device. The relatively complicated components to accomplish this effect may derive improved characteristics by including them in insert devices, which may then be included with standard or similar materials useful in the fabrication of state of the art ophthalmic lenses.

The prevalence of handheld electronic devices with screens and operating systems, including, for example, tablets, smartphones, and eReaders, have prompted an evolution of interfacing mechanisms. For example, some early handheld devices were not operated by interacting with the device screen and often required a stylus pen to interface with a device input pad. Later models included fully interactive screens, allowing users to interface with the device using their fingers or stylus pens.

Similarly, the methods of interacting with non-handheld devices, such as a desktop computer or television, have also evolved to meet the needs of an increasingly diverse population of computer users. For example, some computers had adaptive features to allow quadriplegic users to operate the device, often through use of cameras that could detect eye movements.

Recently, handheld devices have incorporated similar adaptive technology to allow for convenient hands-free operation. However, the integration of eye-tracking technology into a handheld device is very limited. The eye-tracking technology generally utilizes a camera within the device, which may cause misleading eye movement cues, since a handheld device is inherently portable. The combination of device movement, eye movement, and head movement may lead to inconsistent commands.

The control based on eye-movement is limited in functionality as well. Currently, some devices allow for basic scrolling operation, wherein the device recognizes that a user has reached a perimeter of the device screen and that the information on the page extends beyond that perimeter. Some devices recognize when a user has turned away from the device screen, wherein the device will pause the media until the user has returned to viewing the device screen.

Accordingly, there is a need for a more accurate and dynamic eye tracking mechanism, which may allow for broader interfacing capabilities. The tracking and interfacing mechanisms may allow an energizable ophthalmic lens to interface with a range of external devices, including handheld or non-hand-held devices. Accordingly, it may be desirable to improve the process, methods, and devices for interfacing with an external device. It may be anticipated that some of the solutions for effectively interfacing with an external device through energizable ophthalmic lenses may provide novel aspects for non-energized devices and other biomedical devices. Novel methods, devices, and apparatus relating to communication between an energized ophthalmic lens and an external device are therefore important.

SUMMARY OF THE INVENTION

The energizable ophthalmic lens, which may be capable of interfacing with an external device, of the present invention overcomes the disadvantages associated with the prior art as briefly described above. Further, the present invention allows for broader interfacing capabilities than exist with such prior art.

The present invention relates to an energizable ophthalmic lens system comprising at least one ophthalmic lens capable of interfacing with a specified external device, wherein the ophthalmic lens may comprise electronic components and soft lens portion that may at least partially encapsulate the electronic components. Such electronic components may comprise a wireless receiver, a wireless transmitter, a processor, a sensor, and conductive traces that may interconnect the electronic components. Some such ophthalmic lenses may further comprise a power source capable of energizing the electronic components. Alternatively, the ophthalmic lens may be energized wirelessly by the external device. The electronic components may be encapsulated within a media insert.

The electronic components may enable the ophthalmic lens system to interface with a specified external device. Wireless communication may occur once the ophthalmic lens system pairs with the specific external device. The interfacing may allow the ophthalmic lens system to operate the external device or the external device to operate the ophthalmic lens system or both. For example, the interfacing may automatically adjust the brightness of the screen of the external device based on pupil and ambient light data gathered by the ophthalmic lens system and ambient light data gathered by the external device. As another example, the ophthalmic lens system may comprise an event notification mechanism that may notify the user of an event that may occur in or between the ophthalmic lens system and external device.

The external device may be operable through a set of eye gestures, which may comprise deliberate eye movement or lid position change. In some aspects, the ophthalmic lens system may comprise a position detection mechanism, which may be capable of detecting lid position or eye movement. The ophthalmic lens system may transmit such data to the external device. The position data may comprise the eye gestures or may direct operation of the ophthalmic lens system or the external device by other means. For example, the position detection mechanism may track the gaze of the user, which may prompt the external device to scroll.

Some ophthalmic lens systems may comprise a second ophthalmic lens similar to the first ophthalmic lens, wherein the second ophthalmic lens may be worn on the opposite eye of the user. Where both ophthalmic lenses comprise position detectors, the external device may be able to track convergence, which may indicate the viewing distance between the external device and the ophthalmic lens system. Based on convergence data, the external device may increase the size of fonts and images on the screen or, where the ophthalmic lens system comprises a variable optic portion, may adjust the power of the ophthalmic lens system.

The ophthalmic lens system of the present invention offers a dynamic, accurate, and hands-free means to interface with an external device. Such a system may also shift the power and processing burdens from the ophthalmic lenses to the external device, which may be significantly less limited by size and biocompatibility.

BRIEF DESCRIPTION OF THE DRAWINGS

The foregoing and other features and advantages of the invention will be apparent from the following, more particular description of preferred embodiments of the invention, as illustrated in the accompanying drawings.

FIGS. 9A-9D illustrate a top down view of various gaze directions and convergence distances of a pair of eyes each wearing energizable ophthalmic lenses with position recognizing mechanisms.

FIGS. 10A-10D illustrate a top down view of various gaze directions and convergence distances of a pair of eyes, wherein only one eye wears an energizable ophthalmic lens with a position recognizing mechanism.

FIG. 11A illustrates a pair of eyes viewing the screen of an external device with a privacy guard, wherein the user is not wearing energizable ophthalmic lenses with a privacy guard filter.

FIG. 11B illustrates a pair of eyes viewing the screen of an external device with a privacy guard, wherein the user is wearing energizable ophthalmic lenses with a privacy guard filter.

FIG. 12 illustrates a system to automatically adjust the brightness of the screen of an external device.

DETAILED DESCRIPTION OF THE INVENTION

Figure 1A:
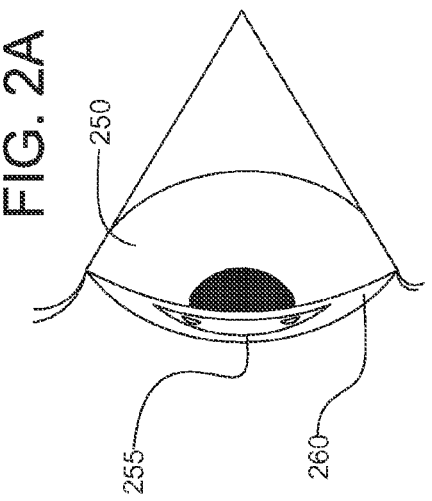
FIG. 1A illustrates a cross sectional view of an exemplary embodiment of an energizable ophthalmic lens on an eye, wherein the energizable ophthalmic lens may be capable of wirelessly interfacing with an external device.

The present invention describes an energizable ophthalmic lens with interfacing capabilities to communicate with an external device. In general, according to some embodiments of the present invention, interfacing and/or position tracking mechanisms may be incorporated into an energizable ophthalmic lens, such as those that may include a media insert.

In the following sections, detailed descriptions of exemplary embodiments of the invention will be given. The description of both preferred and alternative embodiments are exemplary embodiments only, and it is understood that to those skilled in the art that variations, modifications, and alterations may be apparent. It is therefore to be understood that the exemplary embodiments do not limit the scope of the underlying invention.

GLOSSARY

In this description and claims directed to the present invention, various terms may be used for which the following definitions will apply:

Component: as used herein refers to a device capable of drawing electrical current from an energy source to perform one or more of a change of logical state or physical state.

Electrical Communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Encapsulate: as used herein refers to creating a barrier to separate an entity, for example, a media insert, from an environment adjacent to the entity.

Encapsulant: as used herein refers to a layer formed surrounding an entity, such as, for example, a media insert, that creates a barrier to separate the entity from an environment adjacent to the entity. For example, encapsulants may comprise silicone hydrogels, such as Etafilcon, Galyfilcon, Narafilcon, and Senofilcon, or other hydrogel contact lens material. In some exemplary embodiments, an encapsulant may be semipermeable to contain specified substances within the entity and preventing specified substances, for example, water, from entering the entity.

Energized: as used herein refers to the state of being able to supply electrical current to or to have electrical energy stored within.

Energy: as used herein refers to the capacity of a physical system to do work. Many uses within the present invention may relate to the capacity of being able to perform electrical actions in doing work.

Energy Source: as used herein refers to any device or layer that is capable of supplying energy or placing a logical or electrical device in an energized state.

Event: as used herein refers to a defined set of parameters that may occur in a variety of locations, including, for example, an ocular environment, an ophthalmic lens, an environment proximate to the ophthalmic lens, or an external device. For example, an event may comprise a biomarker in the ocular environment, energization level of the ophthalmic lens, a visual recognition of a particular object in the environment proximate to the ophthalmic lens, or the receipt of an email or text by an external device. An event may be specific to a user, such as a level of medication, or may be generally applicable to all user, such as a phone call in an external device.

Functionality: as used herein refers to a fundamental use or purpose of the ophthalmic lens, in contrast to auxiliary or incidental functions. Functionality may comprise, for example, vision correction, active-agent dispensing, cosmetic, external device interfacing, or three-dimensional perception of stereoscopic media. In contrast, incidental functions may comprise actions necessary to allow for operation of the fundamental purpose.

Functionalized: as used herein refers to making a layer or device able to perform a function including for example, energization, activation, or control.

Intraocular Lens: as used herein refers to an ophthalmic lens that may be embedded within the eye.

Ophthalmic lens or ophthalmic device or lens: as used herein refers to any device that resides in or on the eye. The device may provide optical correction, may be cosmetic, or provide some functionality unrelated to optic quality. For example, the term lens may refer to a contact lens, intraocular lens, overlay lens, ocular insert, optical insert, or other similar device through which vision is corrected or modified, or through which eye physiology is cosmetically enhanced (e.g. iris color) without impeding vision. Alternatively, lens may refer to a device that may be placed on the eye with a function other than vision correction, for example, monitoring of a constituent of tear fluid or means of administering an active agent. In some exemplary embodiments, the preferred lenses of the present invention may be soft contact lenses that are made from silicone elastomers or hydrogels, which may include, for example, silicone hydrogels and fluorohydrogels.

Lens-forming mixture or Reactive Mixture or RMM: as used herein refer to a monomeric composition and/or pre-polymer material that may be cured and cross-linked or cross-linked to form an ophthalmic lens. Various embodiments may include Lens-forming mixtures with one or more additives such as UV blockers, tints, diluents, photoinitiators or catalysts, and other additives that may be useful in an ophthalmic lenses such as, contact or intraocular Lenses.

Liquid Crystal: as used herein refers to a state of matter having properties between a conventional liquid and a solid crystal. A liquid crystal cannot be characterized as a solid but its molecules exhibit some degree of alignment. As used herein, a liquid crystal is not limited to a particular phase or structure, but a liquid crystal may have a specific resting orientation. The orientation and phases of a liquid crystal may be manipulated by external forces such as, for example, temperature, magnetism, or electricity, depending on the class of liquid crystal.

Media insert: as used herein refers to an encapsulated insert that will be included in an energized ophthalmic device. The energization elements and circuitry may be embedded in the media insert. The media insert defines the primary purpose of the energized ophthalmic device. For example, in embodiments where the energized ophthalmic device allows the user to adjust the optic power, the media insert may include energization elements that control a liquid meniscus portion in the optic zone. Alternatively, a media insert may be annular so that the optic zone is void of material. In such embodiments, the energized function of the lens may not be optic quality but may be, for example, monitoring glucose or administering medicine.

Optic Zone: as used herein refers to an area of an ophthalmic lens through which a user of the ophthalmic lens sees.

Power: as used herein refers to work done or Energy transferred per unit of time.

Rechargeable or re-energizable: as used herein refers to a capability of being restored to a state with higher capacity to do work. Many uses within the present invention may relate to the capability of being restored with the ability to flow electrical current at a certain rate for certain, reestablished time periods.

Reenergize or recharge: as used herein refers to restoring to a state with higher capacity to do work. Many uses within the present invention may relate to restoring a device to the capability to flow electrical current at a certain rate for certain, reestablished time periods.

Stabilizing Feature: as used herein refers to a physical characteristic that stabilizes an ophthalmic device to a specific orientation on the eye, when the ophthalmic device is placed on the eye. In some exemplary embodiments, the stabilizing feature may add sufficient mass to ballast the ophthalmic device. In some exemplary embodiments, the stabilizing feature may alter the front curve surface, wherein the eyelid may catch the stabilizing feature and the user may reorient the lens by blinking. Such exemplary embodiments may be enhanced by including stabilizing features that may add mass. In some exemplary embodiments, stabilizing features may be a separate material from the encapsulating biocompatible material, may be an insert formed separately from the molding process, or may be included in the media insert.

Substrate Insert: as used herein refers to a formable or rigid substrate that can be capable of supporting an energy source and may be placed on or within an ophthalmic lens. In some exemplary embodiments, the substrate insert also supports one or more components.

Three-dimensional perception or three-dimensional viewing: as used herein refers to where an ophthalmic device translates a two-dimensional image so that the brain interprets three-dimensional properties within the image.

Three-dimensional surface or three-dimensional substrate: as used herein refers to any surface or substrate that has been three-dimensionally formed where the topography is designed for a specific purpose, in contrast to a planar surface.

Variable Optic: as used herein refers to the capacity to change an optical quality, such as, for example, the optical power of a lens or the polarizing angle.

Ophthalmic Lens

An energizable ophthalmic lens may interface with a spectrum of electronic external devices, including, for example, watches, smartphones, televisions, and computers. In some preferable embodiments, the external device may comprise an operating system and/or a screen, which may allow for complex interfacing capabilities.

Figure 2A:
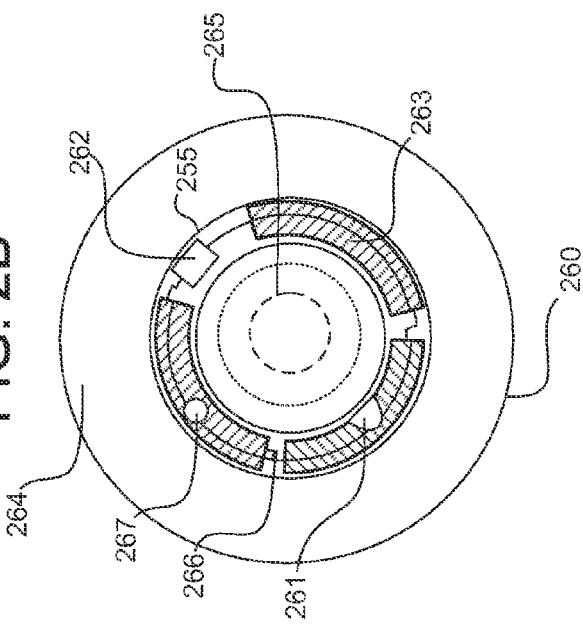
FIG. 2A illustrates a cross sectional view of an alternate embodiment of an energizable ophthalmic lens on an eye, wherein the energizable ophthalmic lens may be capable of wirelessly interfacing with an external device.
Figure 1B:
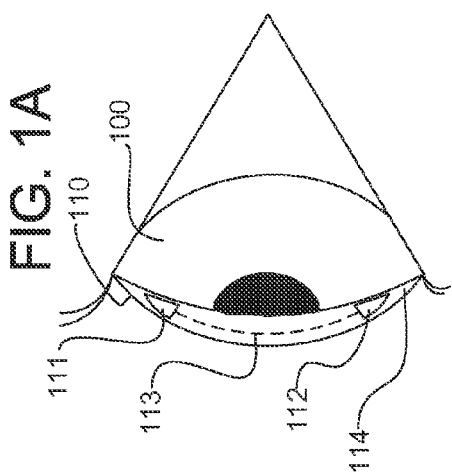
FIG. 1B illustrates a front view of an exemplary embodiment of an energizable ophthalmic lens capable of wirelessly interfacing with an external device.
Figure 2B:
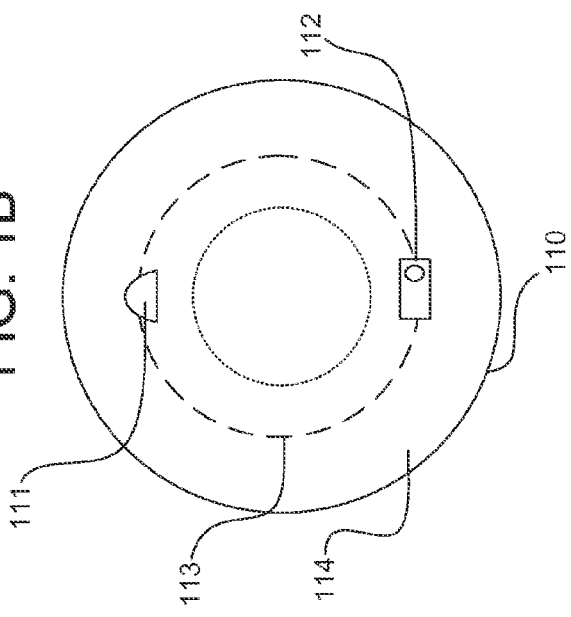
FIG. 2B illustrates a front view of an alternate embodiment of an energizable ophthalmic lens capable of wirelessly interfacing with an external device.

Referring to FIGS. 1A and 2A, exemplary embodiments of an energizable ophthalmic lens 110, 260 with interface capabilities with an external device are illustrated on an eye 100, 250. FIGS. 1B and 2B illustrate a front view of the ophthalmic lenses 110, 260. As shown in FIGS. 1A and 1B, an ophthalmic lens 110 may comprise a soft biocompatible portion 114, a processor with a receiver and/or transmitter 112, and conductive traces 113.

Some aspects may comprise additional electronic components 111 that may add to the functionality of the ophthalmic lens. For example, the electronic component 111 may comprise an event notification mechanism, wherein a prompt from the external device may activate the event notification mechanism, such as through use of a light emitting diode, vibration, or sound device. The notification mechanism may be activated when an event, such as a phone call or incoming email, may occur on the external device; when an event, such as an energization, may occur on the ophthalmic lens; or when an event, such as a successful pairing, may occur between the ophthalmic lens and the external device. For exemplary purposes, the electronic component 111 may be described as an event notification mechanism, but other functionalities may be practical and desirable. Accordingly, such variations are well within the scope of the inventive art described herein.

In some exemplary embodiments, the ophthalmic lens 110 may not comprise a power source, and the ophthalmic lens 110 may be powered through a wireless energy transmission. For example, placing the ophthalmic lens 110 in a specified proximity to an external device may charge the sensor and the notification mechanism. Alternatively, when an engagement prompt from either the external device or the ophthalmic lens 110 may initiate interfacing between the devices, the external device may wirelessly power the notification mechanism.

The components 111-113 may not be encapsulated in a media insert, and the soft biocompatible portion 114 may be in direct contact with the components 111-113. In such exemplary embodiments, the soft biocompatible portion 114 may encapsulate the components 111-113. The encapsulation may suspend components 111-113 at a specific depth within the ophthalmic lens 110. Alternatively, the components 111-113 may be included on a substrate insert. The substrate insert may be formed and the components 111-113 may be placed on the substrate prior to the addition of the soft biocompatible portion 114.

An alternative exemplary embodiment of a media insert 255 for an energized ophthalmic device 260 on an eye 250 is illustrated in FIG. 2A, and a corresponding energized ophthalmic device 260 is illustrated in FIG. 2B. The Media insert 255 may comprise an optic zone 265 that may or may not provide a second functionality, including, for example, vision correcting. Where the energized function of the ophthalmic device is unrelated to vision, the optic zone 265 of the media insert 255 may be void of material.

In some exemplary embodiments, the media insert 255 may include a portion not in the optic zone 265 comprising a substrate incorporated with energizing elements, such as a power source 263, and electronic components, such as a processor 262. In some embodiments, the power source 263, including, for example, a battery, and the processor 262, including, for example, a semiconductor die, may be attached to the substrate. In some such aspects, conductive traces 266 may electrically interconnect the electronic components 262, 261 and the energization elements 263.

In some exemplary embodiments, the media insert 255 may further comprise a receiver 267, which may wirelessly detect, transmit, and receive interface data to and from an external device. The receiver 267 may be in electrical communication, such as through the conductive traces 266, with the processor 262 and the power source 263.

In some exemplary embodiments, the processor 262 may be programmed to establish the parameters of the functionality of the ophthalmic lens 260. For example, where the ophthalmic lens 260 comprises a variable optic portion in the optic zone 265, the processor may be programmed to set the energized optical power. Such an exemplary embodiment may allow for mass production of media inserts that have the same composition but include uniquely programmed processors.

The processor may be programmed before the encapsulation of the electrical components 261-263, 266, 267 within the media insert 255. Alternatively, the processor 262 may be programmed wirelessly after encapsulation. Wireless programming may allow for customization after the manufacturing process, for example, through a programming apparatus in a doctor's office, a store, or a home. In some exemplary embodiment, the external device may be capable of programming an ophthalmic lens.

For illustrative purposes, the media insert 255 is shown in an annular embodiment, which may not include a portion in the optic zone 265, although several possibilities may exist for the mechanical implementation of a functional insert. However, where a functionality of the media insert 255 may be related to vision, the media insert 255 may include an energizable element within the optic zone 265. For example, the media insert 255 may comprise a variable optic portion, wherein the media insert 255 may provide multiple powers of vision correction based on different energization levels. In some exemplary embodiments, the external device may comprise a control mechanism for the variable optic portion, or other adjustable functionalities.

The media insert 255 may be fully encapsulated to protect and contain the energization elements 263, traces 266, and electronic components 261, 262 and 267. In some embodiments, the encapsulating material may be semi-permeable, for example, to prevent specific substances, such as water, from entering the media insert 255 and to allow specific substances, such as ambient gasses or the byproducts of reactions within energization elements, to penetrate or escape from the media insert 255.

In some exemplary embodiments, the media insert 255 may be included in an ophthalmic device 260, which may comprise a polymeric biocompatible material. The ophthalmic device 260 may include a rigid center, soft skirt design wherein a central rigid optical element comprises the media insert 255. In some specific embodiments, the media insert 255 may be in direct contact with the atmosphere and the corneal surface on respective anterior and posterior surfaces, or alternatively, the media insert 255 may be encapsulated in the ophthalmic device 260. The periphery 264 of the ophthalmic device 260 may be a soft skirt material, including, for example, a polymerized reactive monomer mixture, such as a hydrogel material.

Figure 3:
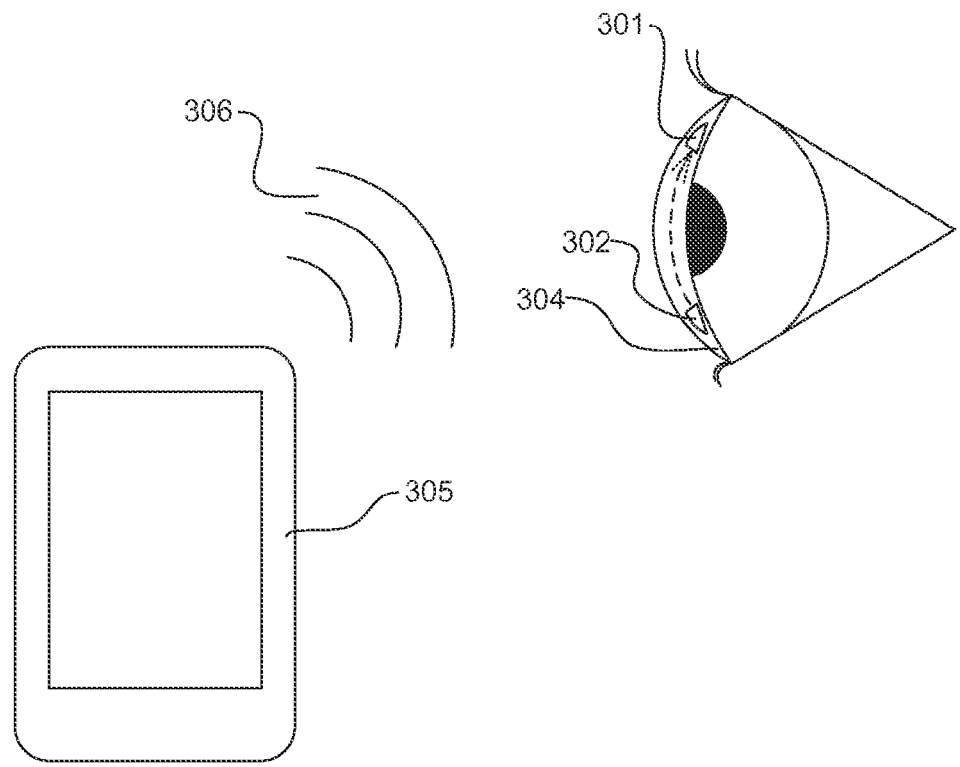
FIG. 3 illustrates an exemplary embodiment of wireless communication from an external device to an energizable ophthalmic lens on an eye.
Figure 4:
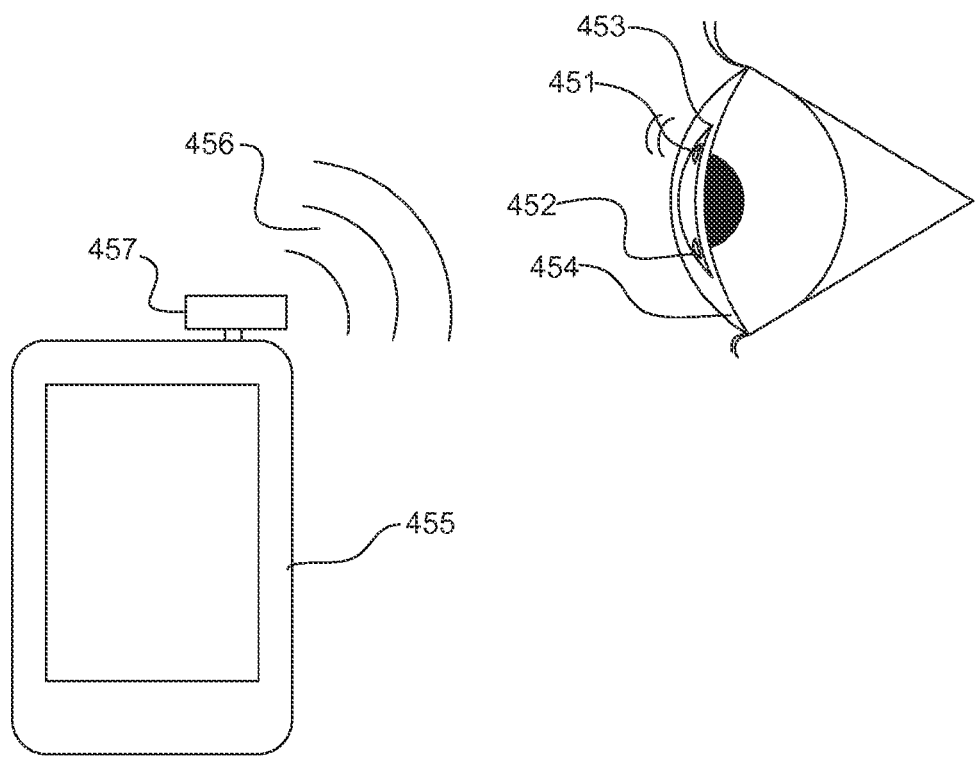
FIG. 4 illustrates an alternate embodiment of wireless communication from an external device to an energizable ophthalmic lens on an eye.

Referring now to FIGS. 3 and 4, exemplary embodiments of wireless communication from an external device to an energizable ophthalmic lens on an eye are illustrated. In accordance with one exemplary embodiment, an external device 305 may transmit interface data or prompts 306 to a receiver 302 on the ophthalmic lens 304. In some exemplary embodiments, the transmitted interface data 306 may trigger an activation of a notification mechanism 301. For example, as shown, the notification mechanism may comprise a light source, wherein the interface data 306 may prompt illumination. In such exemplary embodiments, the light source may be directed at the eye. Alternatively, the light source may be directed into the ophthalmic lens 304, wherein the ophthalmic lens 304 may reflect or disperse the light. An indirectly visible light may soften the light to a glow, which may be less jarring visually.

In some alternative exemplary embodiments, an external device 455 may include a transmission adapter or dongle 457, which may allow the external device 455 to wirelessly transmit and receive interface data 456 to and from the receiver 452. This implementation may be preferred, for example, if the wireless protocol necessary to communicate with the receiver 452 is not implemented in the external device 455. For example, the design constraints on the ophthalmic device 454 may require the use of a custom low-power communication protocol.

The receipt of the external device interface data 456 may activate a notification mechanism 451. For example, the notification mechanism may comprise a vibration generation device for providing mechanical movement, including, for example, a piezoelectric device. Such a mechanism may be more jarring than a light source.

Accordingly, a vibration embodiment may be preferable where the interface data 456 may prompt an affirmative action from the user, such as blink recognition of the notification. Some exemplary embodiments may include multiple notification types. For example, the default notification may be a flashing light, and the user may assign the vibration notification to a specific event, including, for example, a phone call or text message from a specific contact or appointment reminders, where the external device may comprise a smartphone. As another example, a light notification may provide confirmation to the user that the ophthalmic lens is successfully paired with the external device.

In still further exemplary embodiments, the notification mechanism 451 may comprise a sound generation device, wherein the sound may be audible to the user, for example, through bone conduction. The sound may be audible based on the proximity of the eye to the skull through the eye socket, wherein the bones of the skull may direct the sound to the cochlea. In some such aspects, the sound generation device may comprise a transducer, wherein the transducer may convert the wirelessly received data to an acoustic output.

The sound may be determined by the notification mechanism, wherein external device interface data may trigger a preprogrammed sound, such as a beep. Alternatively, the external device interface data may include the specific ringtone or sound associated with that external device event. In such exemplary embodiments, the notification mechanism may generate the specific ringtone or sound, allowing the user to discern between callers or events, even while the external device may be on a silent setting. A controller in the ophthalmic device 454 may store several notification methods, for example light flashing, vibration, and sound patterns, which may be selected by communication 456 instead of being transmitted across communication 456.

For illustrative purposes, in the exemplary embodiment where the notification mechanism 301 comprises a light source, the energizable elements 301 and 302 are shown as components separately encapsulated in the ophthalmic lens 304. In the exemplary embodiments where the notification mechanism 451 comprises a vibration alert, the energizable elements 451 and 452 are shown as components of a media insert 453. However, variations in notification mechanisms may not be limited to the illustrated embodiments; other exemplary embodiments may be practical and should be considered within the scope of the inventive art.

The external device and the ophthalmic lens may comprise complementary communication protocols enabling the two devices to wirelessly communicate. In some exemplary embodiments, the communication protocol may comprise a non-typical technology for an external device, including, for example, infrared, and the functioning may rely on proximity, which may limit inadvertent wireless communication with unintended external devices.

In such exemplary embodiments, the non-typical technology may be specifically equipped on the external device through additional hardware, including, for example, a transmission adapter or dongle 457. In some exemplary embodiments, the transmission adapter 457 may comprise a wireless protocol specifically designed to allow for asymmetric communication and data exchange between an ophthalmic lens and an external device. Such asymmetrical communication may shift the processing and power burden from the ophthalmic lens to the external device, which may not be as limited in size.

As an illustrative example, the transmission adapter 457 may allow the external device 455 to transmit and receive the external device interface data 456 through an infrared transmission to the receiver 452. Prior to use, the transmission adapter 457 may be paired with the specific ophthalmic lens, for example, where the transmission adapter is calibrated to specific infrared wavelengths or pulse patterns. As is common in digital communication, device addressing, error correction, and encryption may be included in the communication protocol.

Other aspects may allow pairing between the ophthalmic lens and the external device through technology typically included in a standard external device, for example, Bluetooth technology. Unlike infrared, Bluetooth technology is relatively common in external devices, and synchronization may not require additional hardware.

The communication protocol may comprise a low power embodiment, including, for example, ANT or ZigBee technology. This may allow the ophthalmic lens to periodically sample the environment for the external device event data transmission from the external device while also limiting the power loss from the sampling. Low power wireless protocol may generally extend the potential energizable duration of the ophthalmic lens. Complementary wireless protocol profiles may limit the ophthalmic lens to receive transmissions from the intended external device.

In some exemplary embodiments, the pairing may occur prior to use. For example, the ophthalmic lens may be preprogrammed to interact with a specific external device, such as through use of application software that may be downloaded onto the intended external device. In other such exemplary embodiments, the ophthalmic lens may include a serial authentication code or electronic pedigree (e-pedigree), which may be unique to a particular ophthalmic lens or an ophthalmic lens pack. The unique code identifying the ophthalmic lens may vary depending on the serialization methods associated with the brand or line of ophthalmic lenses.

The external device may be programmed to recognize a specific serial code. In some exemplary embodiments, the user may program the external device utilizing capture technology to scan or photograph a stock keeping unit (SKU) barcode or quick response (QR) bar code, which may be associated with the authentication serial number. In some such aspects, the SKU or QR barcode may be located on the packaging of the ophthalmic lens, for example, on the individual blister package or on the box for multiple blisters packages, or other common packaging techniques. Initiating the pairing through interaction with the packaging may be preferable over direct interaction with the ophthalmic lens as a means to reduce contamination of or damage to the ophthalmic lens or the eye.

In some exemplary embodiments, the scanned code may specify the identifying attribute of the ophthalmic lens. The identification may allow the external device to communicate specifically with the intended ophthalmic lens. For example, the scanned code may include the authentication code, the Bluetooth profile, infrared wavelength, or infrared signal pattern, depending on the wireless communication technology.

Prior to a communication between the ophthalmic lens and an external device, the two devices may trade or recognize the serial authorization or e-pedigree, for example, through use of a radio frequency identification system. In some exemplary embodiments, an external device event may trigger the external device to transmit an identification or authorization interrogation to the ophthalmic lens. The interrogation may include all, part, or none of the authorization code. For example, the external device may transmit the entire code, and, where the code matches the serial code of the ophthalmic lens, the lens may transmit a response, which may include the serial code or recognition of the correct serial code.

Alternatively, the interrogation may include a portion of the serial code, and the ophthalmic lens may respond with the remaining portion. A successful string may permit further wireless communication. In still further alternatives, the interrogation may not transmit any portion of the serial code but may prompt the ophthalmic lens to transmit the entire code. Where the external device verifies the serial code, wireless communication may continue, and where the serial code does not match, wireless communication may be terminated.

In some exemplary embodiments, the pairing may occur entirely on eye, wherein a user or external device operator may place the external device in proximity to the ophthalmic lens. Utilizing a software application, including, for example, a downloadable mobile application or standard wireless software installed during manufacturing, the user may prompt the external device to scan for the wireless profile or protocol of the ophthalmic lens. Such an initial scan may pair the external device to the ophthalmic lens, such as, for example, through infrared or Bluetooth technology. Future wireless communication may occur where the external device verifies the identity of the ophthalmic lens based on the pairing.

As an illustrative example, Radio Frequency Identification (RFID) may be utilized as a means to verify the identity of the ophthalmic lens. Verification through RFID may not require the external device to be in the line of the sight of the ophthalmic lens. Such embodiments may limit wireless communication to specific range but not necessarily to a specific location. For example, the external device may be located in a bag or pocket, and wireless communication may still occur where the external device is within range.

An RFID system may also allow for low power requirements for identification exchange based on the type of tag and reader. In some exemplary embodiments, the ophthalmic lens may include a passive tag, wherein the ophthalmic lens may reply to interrogations from an active reader in the external device. Such an embodiment may conserve power use within the ophthalmic lens. In some such aspects, the interrogation may prompt the ophthalmic lens to begin sampling the defined environment for the external device event data. The ophthalmic lens may be inactive prior to the interrogation, and the sampling may be deactivated after a specified amount of time to conserve energy, for example, when the authentication code is not verified. Alternatively, the ophthalmic lens may sample at different rates that may vary based on the presence and interfacing demands of an external device.

Figure 5A:
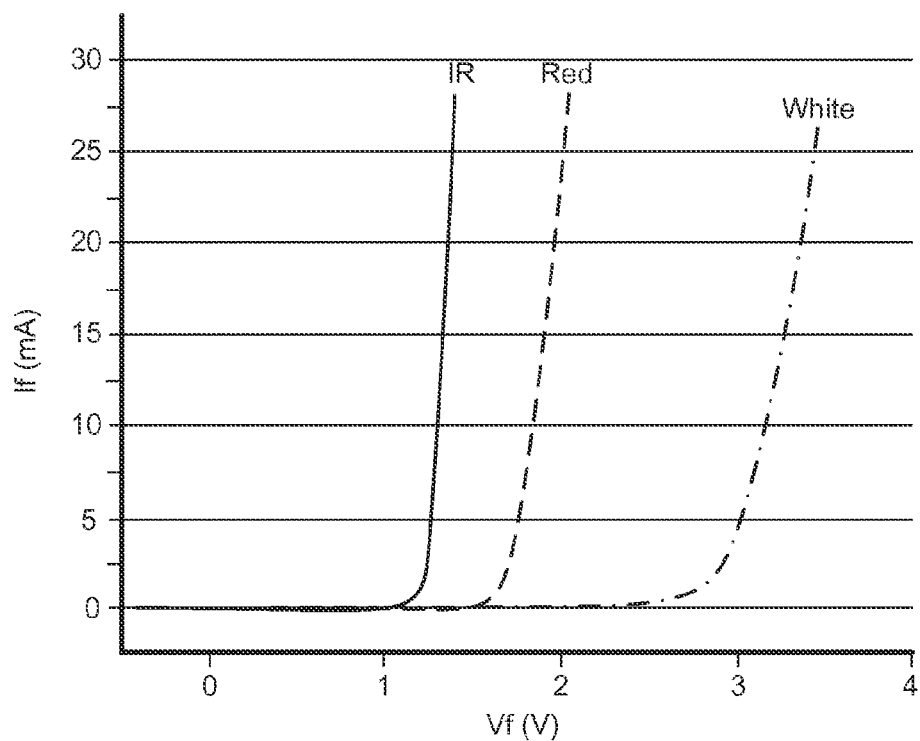
FIG. 5A illustrates a graph representative of current vs. voltage "IV" plots for commercially available light-emitting diodes (LEDs).

Referring now to FIG. 5A, a graph representative of current versus voltage "IV" plots for commercially available light-emitting diodes (LEDs) is illustrated. Three colors, red, white, and infrared (IR), are shown to illustrate the differences in forward voltage associated with various colors. As is known in the art, the differences in forward voltage with light wavelength arise because of the different semiconductor materials, and the bandgaps of those materials, used to make various colors of LEDs. In FIG. 5A, the currents through a red, white, and IR LED are shown on the y-axis plotted against the forward voltage applied across the LEDs. At a given point of comparison, for example 1.0 mA, a certain forward voltage (1.8V) is required to attain the current of interest for a red LED. Likewise, there is a correlation between the LED current and emitted light intensity; accordingly, it should be apparent that sufficient voltage is required to achieve useful brightness from an LED. Similarly, the turn-on voltage for a white and an IR LED are 2.8V and 1.3V, respectively.

In an electronic ophthalmic device, size constraints limit the available area and volume for the battery. These limitations, along with others in ophthalmic devices such as safety and biocompatibility concerns, potentially constrain the battery voltage, instantaneous current, equivalent series resistance, and capacity. Because of limited battery voltage and for other reasons, such as agreement with digital circuit voltage in certain semiconductor fabrication nodes, it may be desired in electronic ophthalmic devices to use low-voltage batteries. Also, rather than using two batteries in series to attain higher voltage, it may be desired to use a single cell, limiting the battery voltage. A single battery may have advantages in manufacturing, reliability, yield, and current capacity over two cells in series.

The limited voltage provided by a single battery cell may be insufficient to activate some types of LEDs, such as those illustrated in FIG. 5A, used for indication, communication, and other applications in an electronic ophthalmic device. For example, an alkaline battery may have 0.8 to 1.6 volts per cell over the useful battery discharge range. Such a cell may have enough voltage to activate a red or IR LED when fully charged and over a portion of the discharge curve, but even these relatively low-voltage LEDs may not activate near the end of the battery discharge. It is important to note that, because of the steep response of LED current to forward voltage (reference the equation for LED current), even if little current is desired, such as a few microamps, to be visible, substantial voltage may still be required. From the LED responses shown in FIG. 5A it may also be apparent that a white LED, by virtue of a 2.8V forward voltage, cannot be activated from a battery with a maximum voltage of 1.6 V.

Because of the aforementioned limitations, there exists the need for a circuit in an electronic ophthalmic device to provide a sufficient voltage to permit LEDs to emit useful light intensity when powered by a low-voltage battery. Such preferable circuits may be small, consume little current, and integrate with circuitry to control LED intensity. Such circuitry may permit the LED intensity to be controlled over a continuously variable range, pulsed, pulse-width modulated, or simply switched on and off.

A charge pump, of which the generic form is well known in the industry, may be used to increase the voltage available from a low-voltage battery. For example, using the case of a battery with minimum voltage of 0.8V when almost fully depleted driving a white LED at 2.8V, the charge pump may be able to multiply the battery voltage by at least 3.5 to achieve sufficiently high output voltage. Further, in some preferable embodiments, the charge pump and associated circuitry may regulate the current through the LED, to regulate LED output intensity. Alternately, a charge pump may sustain the charge in a reservoir or ballast capacitor, and LED control circuitry may then use the ballast capacitor for its supply.

Figure 5B:
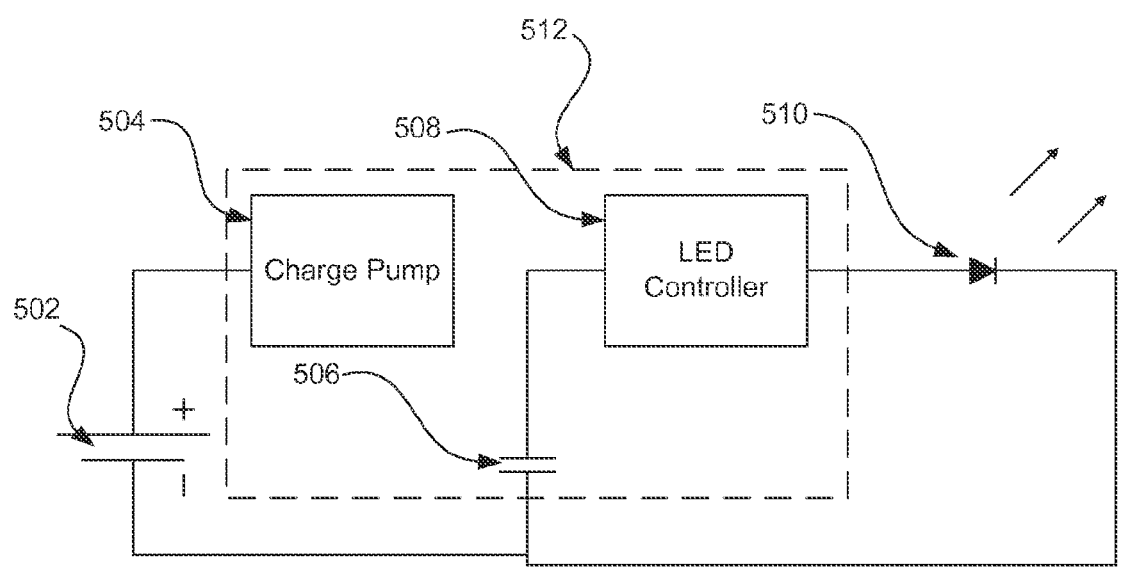
FIG. 5B illustrates a system to drive an LED from a low-voltage battery.

Referring now to FIG. 5B, there is illustrated a system configured to drive an LED 510 from a low-voltage battery 502. In some exemplary embodiments, such as shown, a charge pump 504 may increase the available bias voltage from the battery 502 and may charge a capacitor 506. An LED controller 508 may switch and/or regulate the current to the LED 510. The circuitry of the charge pump 504, capacitor 506, and LED controller 508 may be integrated into the same functional block, which may increase benefits to efficiency and die size. Such integration is indicated by the dashed-line rectangle 512.

Figure 6A:
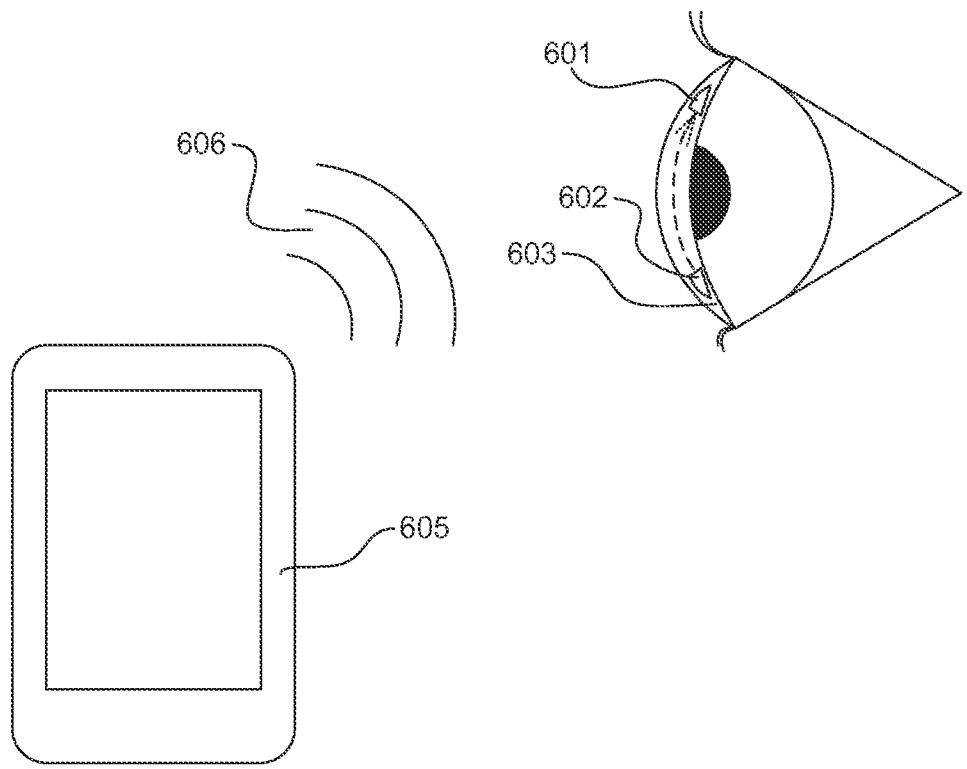
FIG. 6A illustrates a first exemplary embodiment of wireless communication and control between an external device and an energizable ophthalmic lens on an eye.

Referring now to FIG. 6A, exemplary embodiments of wireless communication and control between an external device and an energizable ophthalmic lens on an eye are illustrated. In some exemplary embodiments, an ophthalmic lens 603 may comprise a wireless receiver 602 capable of receiving interface data 606 and a functionality mechanism 601, such as a notification mechanism capable of prompting or notifying the user of an event. In a receiving step, an external device 605 may wirelessly transmit the interface data 606 to the receiver 602.

Figure 6B:
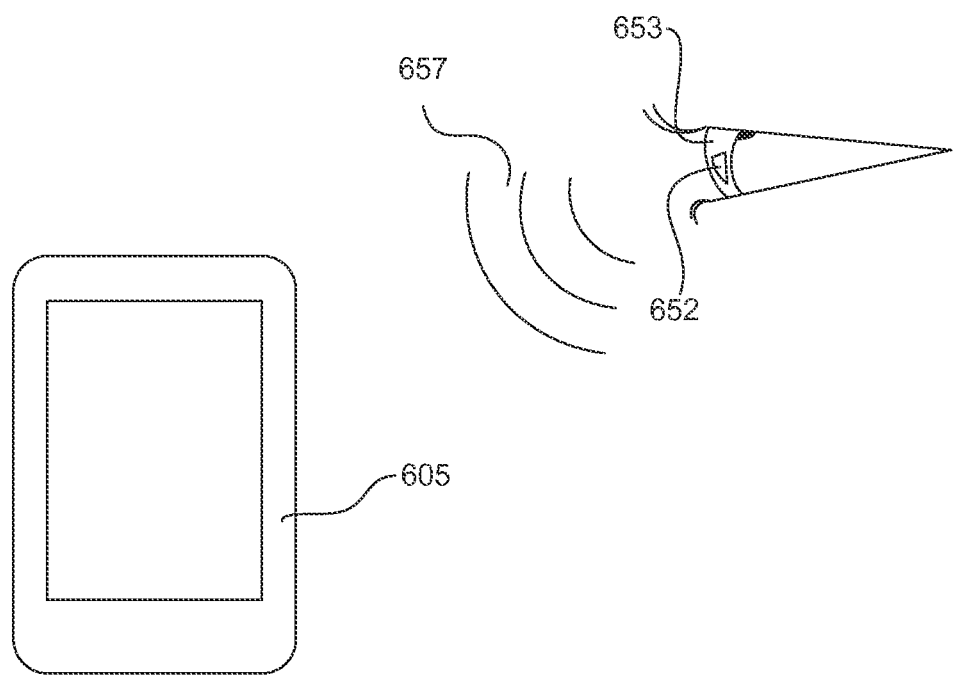
FIG. 6B illustrates a second exemplary embodiment of wireless communication and control between an external device and an energizable ophthalmic lens on an eye.

In some exemplary embodiments, an ophthalmic lens 653, as illustrated in FIG. 6B, may further comprise a transmitter 652, which may be located in a similar position within the ophthalmic lens 653 as the receiver 602, described above with respect to FIG. 6A. In a transmitting step, the transmitter 652 may send response data 657 back to the external device 605. The response data 657 may trigger an action in the external device 605, including, for example, silencing a ringtone. In some further exemplary embodiments, the ophthalmic lens 653 may initiate exchange of interface data. Such initiation may be automatic based on predefined events on the ophthalmic lens or may be user operated, for example, blinking.

In such exemplary embodiments, a verification step, similar to that described with respect to FIGS. 3 and 4, may be preferable to confirm that the wireless communication is between the designated ophthalmic lens 653 and external device 605. The verification step may occur immediately before the transmission of the response or initiation data 657, which may limit misdirected response cues. In other exemplary embodiments, the wireless communication may be continuous throughout the interface data exchange, after the initial transmission of the interface data 606. Where the wireless communication is continuous, a second verification process may not be necessary to ensure the intended wireless communication.

Figure 7:
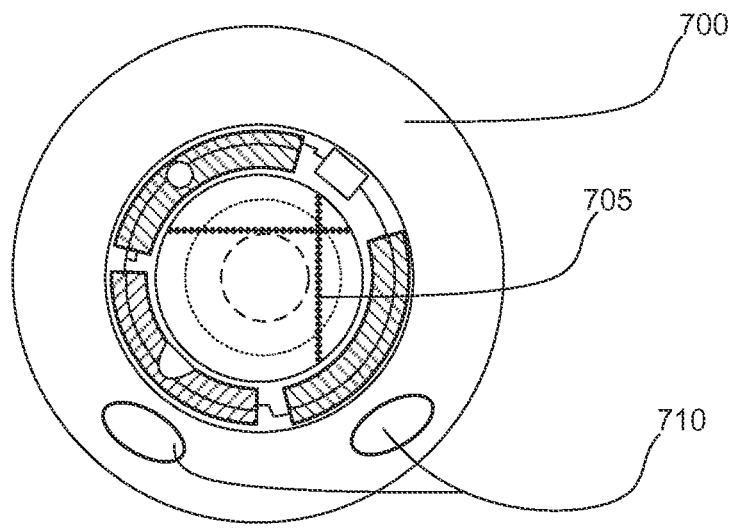
FIG. 7 illustrates an exemplary embodiment of an energizable ophthalmic lens with a position recognizing mechanism.
Figure 8:
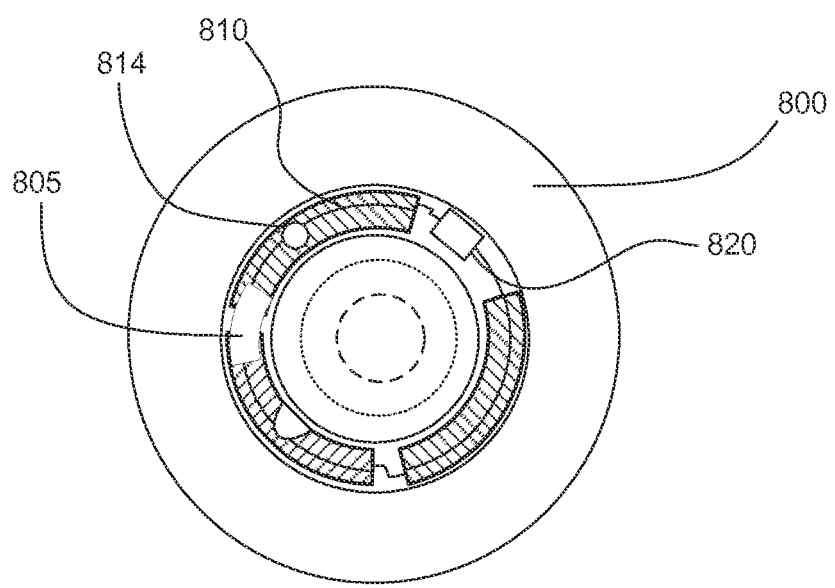
FIG. 8 illustrates an alternate embodiment of an energizable ophthalmic lens with a position recognizing mechanism

Referring now to FIGS. 7 and 8, there is illustrated exemplary energizable ophthalmic lenses 700, 800 with position recognizing mechanisms 705, 805. Pupil position and convergence detection systems 705, 805 incorporated within ophthalmic lenses 700 and 800 and which are positioned on eyes, may track the position of the pupils, the ophthalmic lenses 700 and 800, or both. For example, the detection system may comprise reverse-facing photodetectors capable or observing pupils or accelerometers capable of tracking the movement of the eyes.

As illustrated in FIG. 7, the position recognizing mechanism 705 may detect eye movement behind the ophthalmic lens 700 and/or may detect lid position in front of the ophthalmic lens 700. In some exemplary embodiments, the ophthalmic lens 700 may comprise a sensor array 705. Where the ophthalmic lens 700 may detect lid position, the sensor array 705 may comprise one or more photosensors. Such photosensors may be placed in suitable locations on the ophthalmic lens 700 to provide enough sample locations to reliably determine lid position without obstructing the clear optic zone. For example, as illustrated, a perpendicular line of sensors may be arranged outside of the optic zone.

When an eye is in an open position, all or most of the photosensors may be exposed to receive ambient light, which may create a photocurrent detectable by an electronic circuit included in the ophthalmic lens. A change in lid position may limit ambient light exposure for some or all of the photosensors. The ophthalmic lens may be able to detect lid position based on varying levels of photocurrent.

A lid detection device may allow the ophthalmic lens to recognize eye gestures that may comprise deliberate blink or wink patterns, for example, described with respect to FIG. 6. In some preferable embodiments, lid detection may be combined with convergence detection. Such combinations may allow the ophthalmic lens to discern deliberate lid position from unintentional lid position change, which may be caused, for example, by changing focus between objects of varying distances.

In some exemplary embodiments, a photodetector array 705 may be rear facing, allowing the ophthalmic lens 700 to track gaze. The light to the photodetector may be blocked when located outside of the pupil. When the eye may change gaze, a portion of the photodetectors 705 may be exposed to light reflected through the pupil. Accordingly, the ophthalmic lens 700 may comprise stabilizing features 710, which may allow the eye to move behind the ballasted ophthalmic lens 700.

As illustrated in FIG. 8, the pupil position and convergence detector systems 805 may comprise several components, which may form a more complex system, including, for example, a three-axis accelerometer 805, a power supply 810, a transceiver 815, and a controller 820 comprising signal-conditioning circuitry and memory. A communication channel between the two ophthalmic lenses may allow the pupil position and convergence detection systems to synchronize on pupil position.

In some exemplary embodiments, the ophthalmic lens 800 may move with the eye. In such embodiments, the ophthalmic lens 800 may comprise one or more accelerometers 805. In some such embodiments, the accelerometers 805 may comprise piezoelectric, piezoresistive, or capacitive components, comprising, for example, piezoceramic or crystal. The accelerometers 805 may comprise a micro electro-mechanical system (MEMS). In others, such as illustrated in FIG. 7, the ophthalmic lens 700 may be ballasted by stabilization features 710, wherein the eye may move behind the lens 700.

Some exemplary embodiments may comprise a single energizable lens, wherein the user may wear a passive lens on the opposite eye, or, where vision correction may not be necessary, the user may not wear a second lens. Where vision correction may be necessary, a static vision-correcting power may be included with the energizable lens. Alternatively, the interfacing may require relative information from two energizable lenses, such as, for example, where the device may track gaze, convergence, or both. In such embodiments, the user may need to wear two energizable ophthalmic lenses.

Referring now to FIGS. 9A-9D, various gaze directions and convergence distances of a pair of eyes each wearing energizable ophthalmic lenses are illustrated in a top down view. For illustrative purposes, the screen of the external device is shown in a parallel position to the gaze, but other angles may be practical and should be considered part of the inventive art described herein. Where a user is wearing a set of energizable ophthalmic lenses, the external device may receive positional input from both lenses.

As shown in FIG. 9A, when the external device 900 is viewed at a far distance, both eyes may be gazing in a similar or same direction, with little convergence. As shown in FIG. 9B, when the external device 900 is viewed at a close distance, the eyes may converge, though still gazing forward. As shown in FIG. 9C, when looking to the left portion of the screen of the external device 900, the left eye may be looking forward, and the right eye may shift to look left. As shown in FIG. 9D, the opposite of FIG. 4C may occur when looking at the right portion of the screen of the external device 900.

Referring now to FIGS. 10A-10D, the same scenarios as illustrated in FIGS. 9A-9D are illustrated in a top down view of a pair of eyes, wherein only the right eye may be wearing an energizable lens 1002, with the screen of the external device shown in parallel to the gaze of the eyes. In contrast to a pair of energizable ophthalmic lenses, a single energizable ophthalmic lens may only provide an external device with the positional data from one eye, without relation to the opposite eye.

As shown in FIG. 10A, when the external device 1000 is viewed at a far distance, both eyes may be gazing in a similar or same direction, with little convergence. As shown in FIG. 10B, when the external device 1000 is viewed at a close distance, the eyes may converge, though still gazing forward. As shown in FIG. 10C, when looking to the left portion of the screen of the external device 1000, the left eye may be looking forward, and the right eye may shift to look left. As shown in FIG. 10D, the opposite of FIG. 10C may occur when looking at the right portion of the screen of the external device 1000.

Unlike in FIGS. 9A-9D, the external device 1000 may only receive positional information from the right eye in FIGS. 10A-10D. Accordingly, the device may not be able to discern between FIGS. 10A and 10D or between FIGS. 10B and 10C, since the right eye is in similar positions, though the user may be looking in different directions and distances.

Tracking eye movement may allow the device to recognize precisely where the user is looking and may zoom in on a specific portion of the screen, including, for example, a status bar in a smartphone or tablet. In some exemplary embodiments, a device may be calibrated to the user's preferences and attributes. The calibration may establish the user's eye movement more accurately. The calibration process may provide baseline data to the external device, the ophthalmic lens, or both. In some aspects, the calibration may program the ophthalmic lens to recognize how the lens moves relative to eye movements.

For example, the device may prompt the user to look at specific points at different distances, such as illustrated in FIGS. 9A-9D and 10A-10D. The device may prompt the user to read a screen normally to detect the user's natural reading speed, allowing the device to discern between glancing at different points on the screen and reading. Action may not be required if the user glances at different points, but the device may scroll as the user reads.

Calibration may allow the external device to discern between deliberate and involuntary eye movement, for example, movement caused by nystagmus. A calibration step may prompt the user to look at an object on the screen of the external device for a predefined length of time. Throughout that time, the external device may record or recognize involuntary movement data, including the speed, direction, and distances from the initial focus point.

Based on the calibration, the external device may be able to recognize and ignore involuntary movement data, treating the data similarly to noise, as is common in electronic devices. For users with severe or problematic nystagmus, calibration may not be sufficient to distinguish between voluntary and involuntary eye movements. In some such exemplary embodiments, specialized ophthalmic lenses, additional software in the external device, or a combination of both may be necessary to adequately overcome the "noise" of involuntary eye movement.

In some aspects, the external device may be able to detect and track gaze and eye convergence of a user. Eye convergence may be particularly useful to determine the proximity of the user's eye to the device. The eye convergence data may prompt a responsive action by the device, which may result in a change of focus on the ophthalmic lens or lenses or may result in a change in appearance on the device screen. For example, the device may recognize that the user is holding the screen at a reading distance. In response, the font on the screen may increase, the ophthalmic lens may change power, or both.

Similarly, the ability to track and detect eye movement and blink patterns may allow the user to operate the device through eye gestures. A common operating mechanism in devices may recognize a predefined set of gestures, wherein a user may touch the screen in a specific manner to prompt an action in the device. For example, pinching the screen may prompt the device to zoom in, and swiping the screen may prompt the device to scroll in the direction of the swipe. In exemplary embodiments where the device may recognize eye movements, blinking, or both, a set of eye gestures may be developed to allow the user to operate the device through deliberate eye movement, blinking, or a combination of both.

In some exemplary embodiments, the functionality of the energizable ophthalmic lenses may require communication between the lenses. For example, the ophthalmic lenses may allow the user to perceive stereoscopic media as three-dimensional, which may allow a user to watch "3-D" films, video games, and shows without requiring "3-D glasses," as is typically required with such media. As non-limiting examples, the external device showing the 3-D media may comprise a television, handheld gaming device, and/or tablet. Some exemplary embodiments may require the lenses to alternately block the user's vision at a speed comparable to the refresh rate of stereoscopic media, which may require complex processing and power. The device may be capable of detecting the refresh rate of the stereoscopic media and may prompt the alternating vision blocking in the ophthalmic lenses.

Such exemplary embodiments that utilize an external device to track gaze and/or convergence may reduce the power and processing burden on the ophthalmic lenses, requiring only the ability to wirelessly exchange small amounts of data and, in some aspects, energize a mechanism that may control a functionality within the lens. The external device may serve as the primary processing and power source for the interfacing mechanisms, which may reduce the burden on the ophthalmic lenses, which are inherently limited in size. Utilizing an external device may allow for communication requiring line of sight, which may not be practical where the bridge of the nose impedes communication between a left and right ophthalmic lens.

Referring now to FIGS. 11A and 11B, two sets of eyes 1100, 1150 are illustrated with one set wearing passive ophthalmic lenses 1102 and one set wearing energizable ophthalmic lenses 1152, wherein both sets of eyes 1100, 1150 are viewing the same device screen 1110. In some exemplary embodiments, the external device may include a screen 1110 with a security or privacy guard or layer, wherein a filter on an ophthalmic lens 1152 may be necessary to view the contents of the screen 1110. As illustrated in FIG. 11A, without a filter, the screen 1110 may be visually blocked, and as illustrated in FIG. 11B, an energizable ophthalmic lens with a filter may allow the user to view the screen 1110 through the filter. The privacy guard settings may be static, which may only require a passive filter in or on the ophthalmic lens.

Alternatively, the privacy guard settings may be adjustable, wherein the filter on an energizable ophthalmic lens may be programmable to accommodate variable guard settings. Variable guard settings may limit the probability that another user's ophthalmic lenses comprise the same filter. The variable guard settings may be programmed by the user or may be randomly generated.

In some exemplary embodiments, the privacy guard may comprise a polarized or tinted screen. Where the privacy guard comprises a polarized screen, the filter may comprise a complementary polarization, wherein the filter's polarization may align with the screen's polarization. Where the privacy guard comprises a tint, the filter may block the absorption of the specific wavelength of the tint color.

The filter in the ophthalmic lens may be activated when viewing the device through the privacy guard, which may prevent the filter from impeding the user's vision when not viewing through the privacy guard. Such a privacy guard may be more convenient, less obvious, and more secure than common screen protection methods such as removable filter sheets.

Referring now to FIG. 12, a system to automatically adjust the brightness of the screen 1250 of an external device 1230 is illustrated. Some external devices 1230 may include a backlit screen 1250 with an adjustable brightness. Some current devices, such as smartphones and tablets, automatically adjust brightness based on preprogrammed parameters, for example, ambient light levels. However, the preprogrammed parameters may limit the effectiveness to those users who may fall within those parameters. Correlating pupil 1201 size changes, screen brightness, and ambient light levels 1205, 1235, 1255 may allow for a personalized evaluation of brightness preferences.

Ambient light levels 1205, 1235, 1255 may be measured by multiple sensors or cameras 1210, 1260, 1240. Existing devices with a brightness auto-adjusting feature measure light in front of the screen and/or behind the device. The light levels 1255 in front of the screen 1250 may be skewed by the brightness emitted by the screen, and the light levels 1235 behind the device 1230 may be skewed by the shadow caused by the device 1230.

Alone, each method may not be sufficient to establish the effective ambient light levels. By including ambient light 1205 onto the eye and parameters of the viewing eyes such as pupil diameter, the display 1250 may be optimized to the user, for example, optimizing for black level and dynamic range or color palette. Detecting light levels from multiple locations may result in a more accurate assessment of the ambient light levels. In some preferable embodiments, the ambient light level may be determined by normalizing the measurements from at least two sensors or cameras in the external device and a sensor or camera in at least one ophthalmic lens 1200. In some aspects, the device may develop a brightness profile for a particular user, which may be universal over multiple devices with screens. Such embodiments may limit calibration requirements to establish brightness preference for each device.

Figure 13:
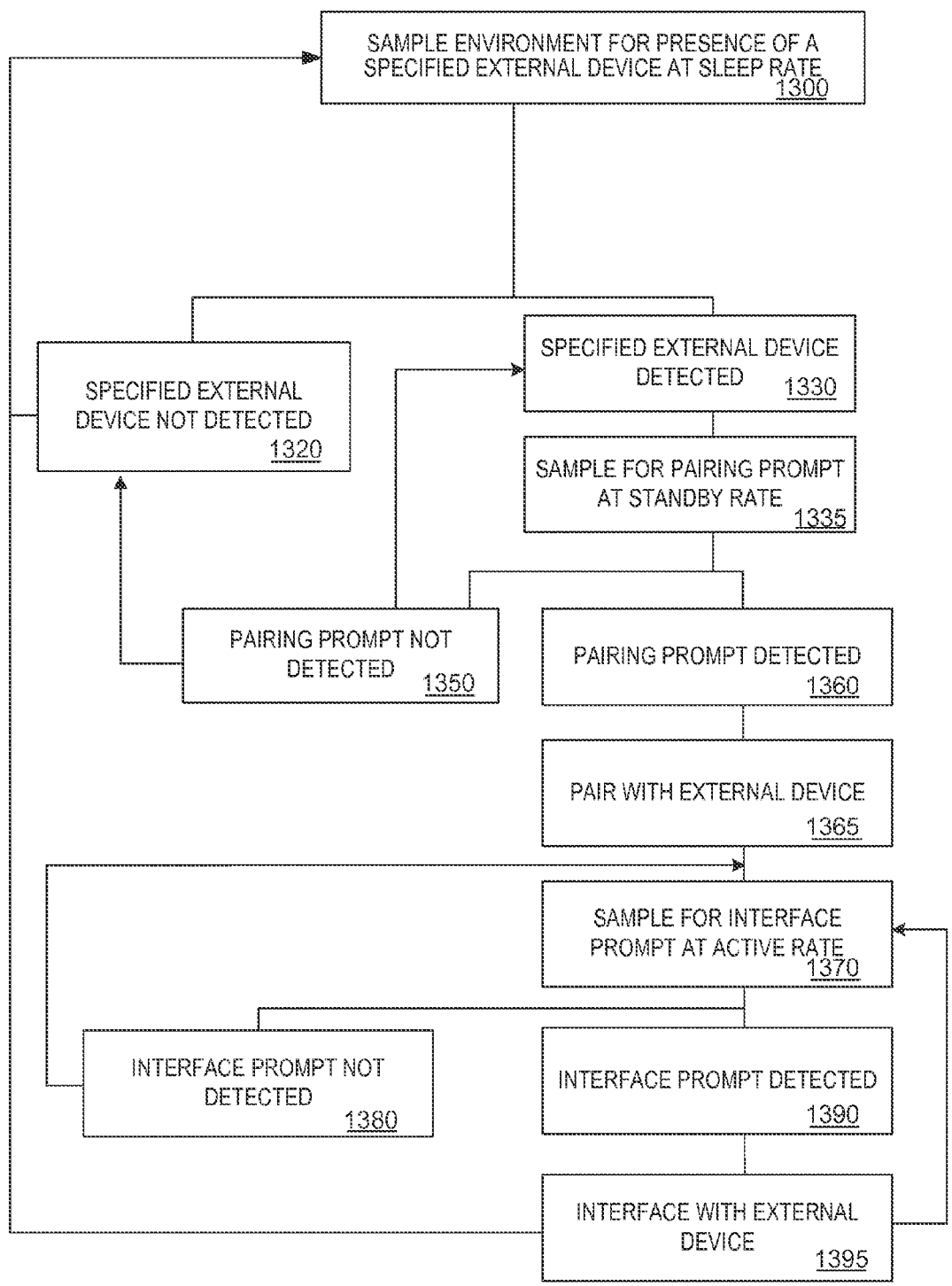
FIG. 13 illustrates a decision flowchart for an energizable ophthalmic lens with variable sample rates.

Referring now to FIG. 13, a decision flow chart for an energizable ophthalmic lens with variable sample rates is illustrated. Variable sample rates may allow the ophthalmic lens to consume power more efficiently than a single sample rate that may be necessary to meaningfully interface with an external device. In some preferable embodiments, the ophthalmic lens may operate at three sample rates or more. The ophthalmic lens may sample at the lowest rate to determine whether a designated external device may be in operable range. Where a designated external device may be detected, the sample rate may increase to determine whether to engage and interface with the external device. The sample rate may be highest when the ophthalmic lens actively interfaces with the external device, which may optimize the user interface. Variable sample rates may limit energy waste.

At 1300, the ophthalmic lens may sample the environment for the presence of a specified external device at a sleep rate, wherein the sleep rate may comprise the slowest sample rate. The sampling at 1300 may detect of the specified external device at 1330 or may not at 1320. Where the ophthalmic lens may not detect the specified external device at 1320, the ophthalmic lens may remain in sleep mode and continue sampling at the lowest rate at 1300. As an example, the sample rate in sleep mode may comprise a frequency between 0.3 and 10 Hz.

Alternatively, where the ophthalmic lens may detect the specified external device at 1330, the ophthalmic lens may begin sampling for a pairing prompt from the specified external device at 1335. At 1335, the ophthalmic lens may sample at standby rate, which may be faster than the sampling rate in sleep mode. For example, the standby rate may comprise a frequency between 2 and 10 Hz. The pairing prompt may initiate communication between the ophthalmic lens and the specified external device.

At 1350, the ophthalmic lens may not detect the pairing prompt, wherein the ophthalmic lens may verify the presence of the specified external device, which may result in detection at 1330 or no detection at 1320. Alternatively, at 1360, the ophthalmic lens may detect the pairing prompt. The detection of the pairing prompt at 1360 may allow the ophthalmic lens to pair with the external device at 1365. In some exemplary embodiments, intermediate steps may occur between the detection step at 1360 and the pairing step at 1365. Such intermediate steps, including, for example, those that will be described with respect to FIG. 14, may comprise a verification or authorization step, which may ensure that the ophthalmic lens communicate with the specified external device.

In response to the pairing at 1365, the ophthalmic lens may begin sampling at an active rate, which may be the highest sampling rate. For example, the active rate may comprise a frequency between 10 and 100 Hz, which may allow interfacing actions to occur without delay that may be caused by a slow sampling rate, such as may occur in sleep or standby. The sampling at 1370 may detect an interface prompt at 1390 or may not at 1380. Where the ophthalmic lens may not detect the interface prompt at 1380, the ophthalmic lens may continue sampling in active rate at 1370, until the pairing may be interrupted, which may trigger a shift down to a lower sample rate, such as, sleep mode at 1300 or standby mode at 1335.

Alternatively, at 1390, the ophthalmic lens may detect the interface prompt and, at 1395, the ophthalmic lens may actively interface with the external device. The ophthalmic lens may continue sampling for the interface prompt at an active rate at 1370. In some exemplary embodiments, after interfacing at 1395, the communication may be interrupted and, at 1300, the ophthalmic lens may return to sleep mode and resume sampling for the presence of the specified external device.

An external device may not be as limited in space and energy as an ophthalmic lens. Accordingly, the external device may sample at a constant and fast rate, wherein the device may detect a data transmission or interface prompt from the ophthalmic lens. In some exemplary embodiments, similarly to the ophthalmic lens, the external device may sample at a lower rate to detect the presence of a compatible ophthalmic lens, wherein the detection may prompt the faster sample rate. For example, the active rate may comprise a frequency between 10 and 100 Hz, and the slower rate may comprise a frequency between 0.3 and 10 Hz.

Figure 14:
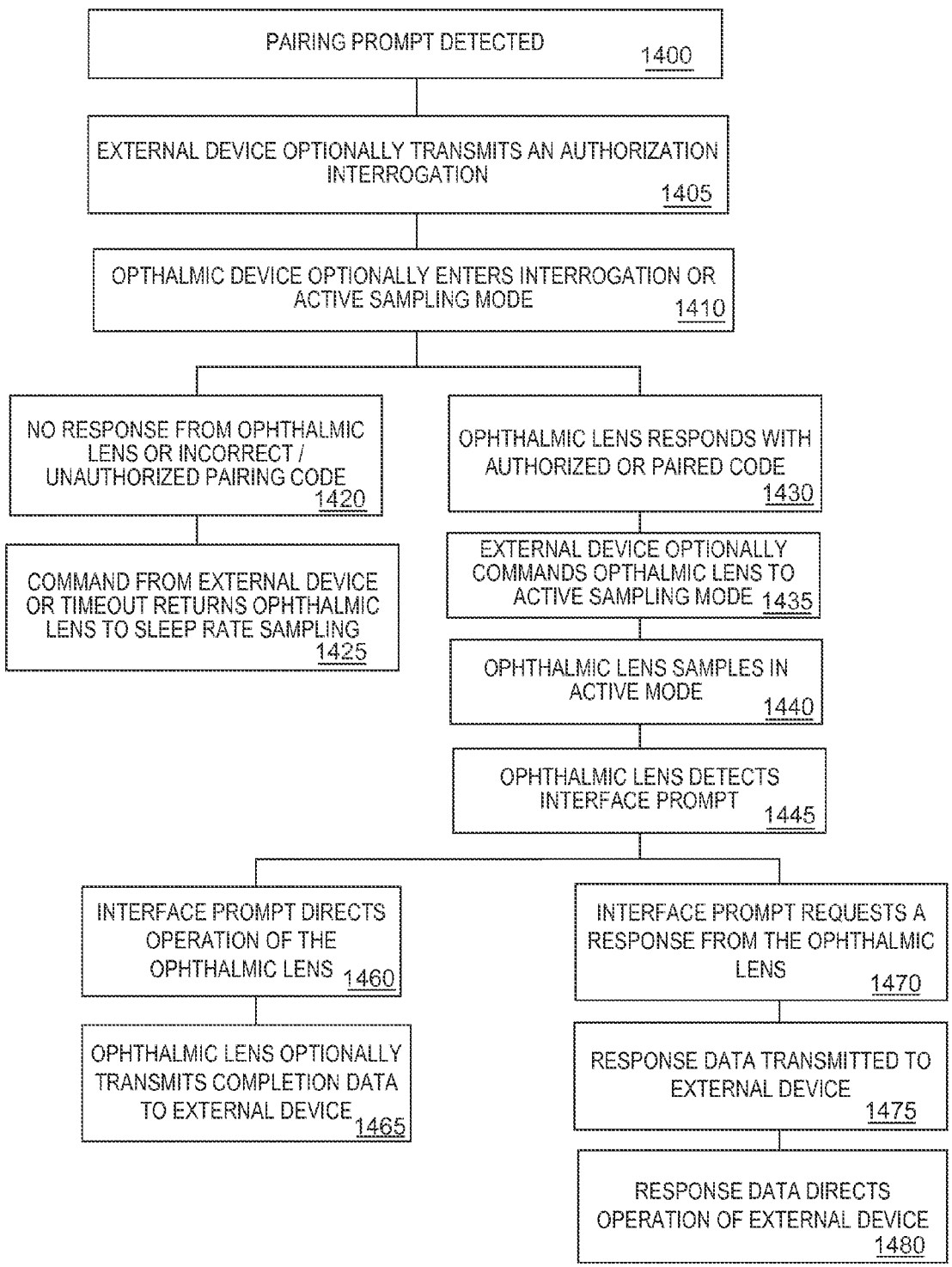
FIG. 14 illustrates the process steps of interfacing between the energizable ophthalmic lens and the external device, once initiated by a pairing prompt

Referring now to FIG. 14, a flowchart illustrates the process steps of interfacing between the ophthalmic lens and the external device, once initiated by a pairing prompt. At 1400, the ophthalmic lens may detect a pairing prompt transmitted by an external device. Optionally, at 1405, the pairing prompt may comprise an authorization interrogation, for example, described with respect to FIG. 4, to the ophthalmic lens, which may respond with an authorization code. In some aspects, at 1410, the pairing prompt may trigger the ophthalmic lens to increase the frequency of sample rate. For example, the ophthalmic lens may enter an interrogation mode, which may comprise a sample rate higher than sleep mode but lower than active mode, or the ophthalmic lens may enter active mode.

In some exemplary embodiments, at 1420, the ophthalmic lens may respond with an unauthorized code or may not respond at all. In such events, at 1425, the ophthalmic lens may return to a sleep sampling rate. At 1425, the external device may command the ophthalmic lens to return to sleep mode based on an incorrect response. A timeout where the external device may not respond within a specified length of time may prompt the ophthalmic lens to return to sleep mode, such as described in FIG. 13.

Where the ophthalmic lens may respond with the authorized or paired code at 1430, the interrogation may pair the external device to ophthalmic lens. In some exemplary embodiments, at 1435, in response to the pairing, the external device may command the ophthalmic lens to active sampling mode. Alternatively, at 1440, the pairing itself may prompt the ophthalmic lens to increase the sample rate to active mode. The sample rate in active mode may be sufficient to allow for effective interfacing between the devices, with a quick response time, preferably almost immediate as perceived by a user.

At 1445, the ophthalmic lens may detect an interface prompt from the external device. At 1460, the interface prompt may direct operation of the ophthalmic lens, wherein the prompt may activate a functionality of the lens. For example, in an ophthalmic lens with a variable optic portion, the interface prompt may trigger a change in vision-correcting power. Similarly, the prompt may trigger an activation of a notification mechanism or a wake-up alert, which may prevent a user from falling asleep while driving. In some exemplary embodiments, at 1465, the ophthalmic lens may transmit completion data back to the external device. The completion data may allow the external device to verify that the interface prompt was received and triggered the correct operation in the ophthalmic lens.

In some exemplary embodiments, at 1470, the interface prompt may request a response from the ophthalmic lens. The requested response may comprise an affirmative action by the user, an action internal to the ophthalmic lens, or a combination of both. For example, the interface prompt may request that the user look at a specific object on the screen or blink in a specified pattern. The ophthalmic lens may then send pupil and/or lid position data back to the external device.

Alternatively, the interface prompt may not require a user response, but may request current positional data from the ophthalmic lens. At 1475, the ophthalmic lens may transmit the response data back to the external device, and at 1480, that response may direct operation in the external device. In still further embodiments, not shown, an interface prompt may direct operation at 1460 and request a response at 1470. The response requested may be a user acknowledgement of the operation, such as an alert or an alarm.

Materials for Insert Based Ophthalmic Lenses

In some exemplary embodiments, a lens type may be a lens that includes a silicone-containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some exemplary embodiments, the ophthalmic lens skirt, which sometimes may be called an insert encapsulating layer, that surrounds the insert may be comprised of standard hydrogel lens formulations. Exemplary materials with characteristics that may provide an acceptable match to numerous insert materials may include the Narafilcon family; including Narafilcon A and Narafilcon B. Alternatively, the Etafilcon family; including Etafilcon A may represent good exemplary material choices. A more technically inclusive discussion follows on the nature of materials consistent with the art herein; but it may be clear that any material which may form an acceptable enclosure or partial enclosure of the sealed and encapsulated inserts are consistent and included.

Suitable silicone containing components include compounds of Formula I

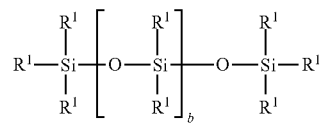

where:

$R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some embodiments between one and 3 $R^1$ comprise monovalent reactive groups.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$ alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one exemplary embodiment b is zero, one $R^1$ is a monovalent reactive group, and at least 3 $R^1$ are selected from monovalent alkyl groups having one to 16 carbon atoms, and in another embodiment from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl]propoxy]propyl ester ("SiGMA"), 2-hydroxy-3-methacryloxypropyloxypropyl-tris(trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another exemplary embodiment, b is 2 to 20, 3 to 15 or in some embodiments 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal $R^1$ comprises a monovalent alkyl group having 1 to 6 carbon atoms and the remaining $R^1$ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another exemplary embodiment b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In one exemplary embodiment, where a silicone hydrogel lens is desired, the lens of the present invention will be made from a Reactive Mixture comprising at least about 20 and preferably between about 20 and 70% wt silicone containing components based on total weight of reactive monomer components from which the polymer is made.

In another exemplary embodiment, one to four $R^1$ comprises a vinyl carbonate or carbamate of the formula:

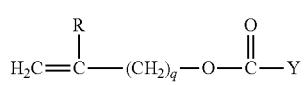

Formula II wherein: Y denotes —O—, —S— or —NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris(trimethylsiloxy)silane]; 3-[tris(trimethylsiloxy)silyl]propyl allyl carbamate; 3-[tris(trimethylsiloxy)silyl]propyl vinyl carbamate; trimethylsilylethyl vinyl carbonate; trimethylsilylmethyl vinyl carbonate, and

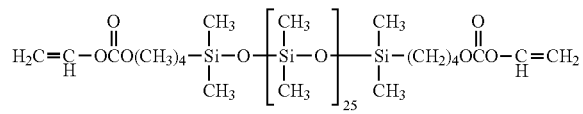

Where biomedical devices with modulus below about 200 are desired, only one $R^1$ shall comprise a monovalent reactive group and no more than two of the remaining $R^1$ groups will comprise monovalent siloxane groups.

Another class of silicone-containing components includes polyurethane macromers of the following formulae:

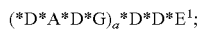

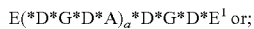

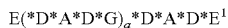

Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

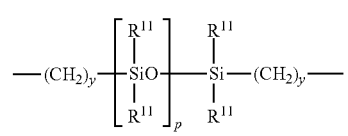

Formula VII $R^{11}$ independently denotes an alkyl or fluoro-substituted alkyl group having 1 to 10 carbon atoms which may contain ether linkages between carbon atoms; y is at least 1; and p provides a moiety weight of 400 to 10,000; each of E and $E^1$ independently denotes a polymerizable unsaturated organic radical represented by formula:

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

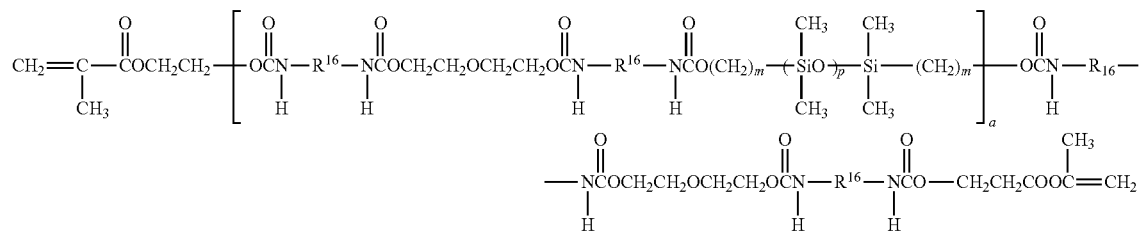

wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

Formula X

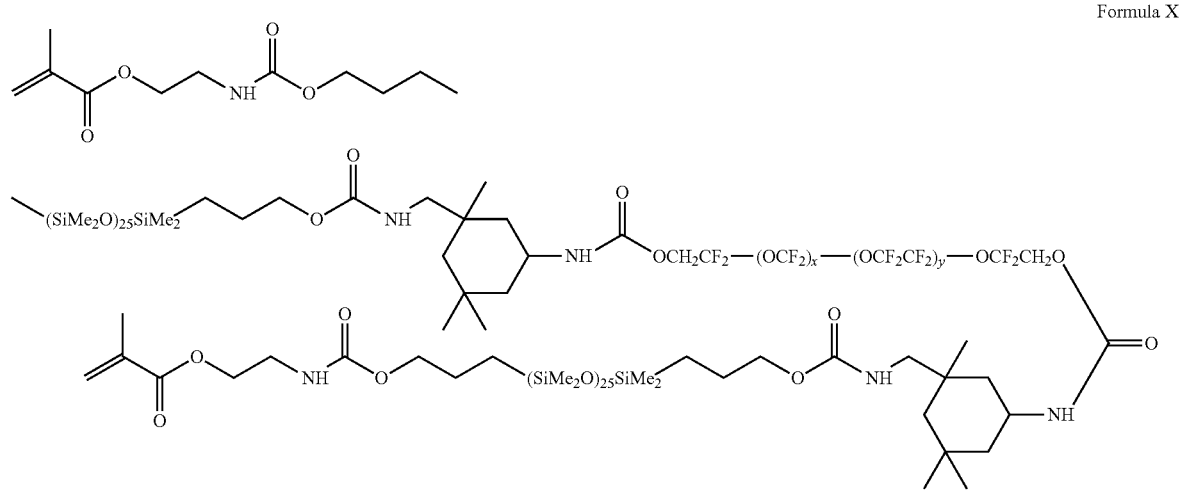

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes may also be used as the silicone-containing component in this invention.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic lens system capable of interfacing with a predefined external device comprising at least a first ophthalmic lens, the first ophthalmic lens comprising:

a first set of electronic components capable of interfacing with the predefined external device;

a first soft lens portion capable of encapsulating at least a portion of the first set of electronic components, wherein the ophthalmic lens system is configured for tracking a gaze of a first eye.

2. The ophthalmic lens system of claim 1, wherein the electronic components comprise:

a receiver configured for wirelessly receiving data from the predefined external device;

a processor in electrical communication with the power source and the receiver, wherein the processor is configured for of controlling the receiver;

a sensor in electrical communication with the processor, wherein the sensor is configured for detecting a user response, and wherein the processor is configured for generating user response data based on the user response;

a transmitter in electrical communication with the processor, wherein the transmitter is configured for transmitting response data to the predefined external device, and wherein the transmitting of response data is capable of triggering a predefined action in the predefined external device; and conductive traces configured for interconnecting the electronic components.

3. The ophthalmic lens system of claim 2, wherein the receiver is capable of wirelessly receiving energy from the predefined external device.

4. The ophthalmic lens system of claim 2, wherein the electronic components further comprise a power source, wherein the conductive traces are configured for electrically connecting the power source with the receiver.

5. The ophthalmic lens system of claim 4, wherein the ophthalmic lens further comprises a media insert configured for encapsulating the electronic components, wherein the soft lens portion is configured for encapsulating at least a portion of the media insert.

6. The ophthalmic lens system of claim 1, wherein the first soft lens portion comprises a polymerized reactive monomer mixture.

7. The ophthalmic lens system of claim 1, wherein a wireless pairing between the first ophthalmic lens and the predefined external device is capable of enabling the interfacing between the ophthalmic lens system and the predefined external device.

8. The ophthalmic lens system of claim 1, wherein the first ophthalmic lens further comprises an event notification mechanism configured for notifying a user of the ophthalmic lens system of a predefined event, wherein the predefined event is detectable by at least one of the ophthalmic lens system or the predefined external device.

9. The ophthalmic lens system of claim 1, wherein at least one of the ophthalmic lens system or the predefined external device is at least configured for of programming or operating a functionality of the predefined external device or a functionality of the first ophthalmic lens.

10. The ophthalmic lens system of claim 1 further comprising a second ophthalmic lens, wherein the second ophthalmic lens comprises:
a second set of electronic components capable of interfacing with the predefined external device;
a second soft lens portion capable of encapsulating at least a portion of the second set of electronic components.

11. The ophthalmic lens system of claim 10, wherein the external device is capable of automatically adjusting a brightness level of a screen of the external device, wherein the brightness level is based on a correlation between one or more a pupil size of a first eye wearing the first ophthalmic lens, a level of brightness of a screen, and a level of brightness of at least a first ambient light.

12. The ophthalmic lens system of claim 11 further comprising a privacy guard filter, wherein the predefined external device comprises a privacy guard configured for limiting view of the screen, and wherein the privacy guard filter is configured for allowing the user to view the screen through the privacy guard.

13. The ophthalmic lens system of claim 12, wherein the ophthalmic lens system is configured for tracking a gaze of the first eye and a second eye wearing the second ophthalmic lens and a convergence between the first eye and the second eye.

14. The ophthalmic lens system of claim 13, wherein a change in the convergence causes an adjustment in object sizes on the screen.

15. The ophthalmic lens system of claim 13, wherein the ophthalmic lens system further comprises a variable optic portion configured for providing a plurality of lens powers through an optic region of the first eye and the second eye, and wherein a change in the convergence causes a change in lens power.

16. The ophthalmic lens system of claim 13, wherein the ophthalmic lens system is capable of transmitting position data to the predefined external device, wherein position data derives from tracking the gaze and the convergence.

17. The ophthalmic lens system of claim 16, wherein the position data comprises the eye gesture capable of triggering an operation in the external device, wherein the eye gesture comprises a deliberate change in the gaze and/or convergence caused by the user.

18. The ophthalmic lens system of claim 17, wherein one or both the first ophthalmic lens and the second ophthalmic lens further comprises an eyelid position detection mechanism capable of detecting an eyelid position of one or both the first eye and the second eye.

19. The ophthalmic lens system of claim 18, wherein the eye gesture further comprises a deliberate change in the eyelid position of one or both the first eye and the second eye.

20. The ophthalmic lens system of claim 11, wherein the first ophthalmic lens further comprises a forward-facing light sensor, wherein the forward-facing light sensor is configured for measuring an ambient light proximate and external to an eye.

21. The ophthalmic lens system of claim 20, wherein the external device further comprises at least a back light sensor and a front light sensor, wherein the back light sensor is configured for measuring an ambient light level external to the external device and in a direction opposite to the screen and the front light sensor is configured for measuring an ambient light level external to the external device and in the direction of the screen.

22. The ophthalmic lens system of claim 21, wherein the first ambient light comprises an overall ambient light level, wherein the overall ambient light level is calculated based on the ambient light measured by the back light sensor, the ambient light measured by the front light sensor, and the ambient light measured by the forward-facing light sensor.

23. The ophthalmic lens system of claim 22, wherein the position data comprises the eye gesture capable of triggering an operation in the external device, wherein the eye gesture comprises deliberate position change caused by the user.

24. The ophthalmic lens system of claim 1, wherein the predefined external device comprises an operating system.

25. The ophthalmic lens system of claim 1, wherein the ophthalmic lens system is configured for sampling data at a plurality of different rates.

26. The ophthalmic lens system of claim 1, wherein the first set of electronic components further comprise a charge pump.

27. The ophthalmic lens system of claim 1, wherein the first ophthalmic lens further comprises a first position detection mechanism configured for detecting eye movement or lid position for the first eye, and wherein the first ophthalmic lens is configured for transmitting position data to the predefined device.

28. The ophthalmic lens system of claim 27, wherein the transmission of the position data is capable of prompting a responsive action in the predefined external device.

* * * * *